US012039223B2

(12) United States Patent
Tsuruga et al.

(10) Patent No.: US 12,039,223 B2
(45) Date of Patent: Jul. 16, 2024

(54) HEAD-MOUNTABLE INFORMATION PROCESSING APPARATUS

(71) Applicant: MAXELL, LTD., Kyoto (JP)

(72) Inventors: Sadao Tsuruga, Kyoto (JP); Yasunobu Hashimoto, Kyoto (JP); Kazuhiko Yoshizawa, Kyoto (JP); Yoshinori Okada, Kyoto (JP)

(73) Assignee: MAXELL, LTD., Kyoto (JP)

( * ) Notice: Subject to any disclaimer, the term of this patent is extended or adjusted under 35 U.S.C. 154(b) by 28 days.

(21) Appl. No.: 17/436,395

(22) PCT Filed: Mar. 4, 2019

(86) PCT No.: PCT/JP2019/008457
§ 371 (c)(1),
(2) Date: Sep. 3, 2021

(87) PCT Pub. No.: WO2020/178961
PCT Pub. Date: Sep. 10, 2020

(65) Prior Publication Data
US 2022/0066733 A1  Mar. 3, 2022

(51) Int. Cl.
*G06F 3/16* (2006.01)
*A61B 5/00* (2006.01)
(Continued)

(52) U.S. Cl.
CPC ............. *G06F 3/165* (2013.01); *A61B 5/021* (2013.01); *A61B 5/02438* (2013.01);
(Continued)

(58) Field of Classification Search
CPC ......... G10L 15/22; G10L 25/51; G10L 15/26; G10L 2015/223; G10L 21/043;
(Continued)

(56) References Cited

U.S. PATENT DOCUMENTS 10,070,034 B2 * 9/2018 Hirabayashi ............. H04N 5/77
11,217,237 B2 * 1/2022 Usher ...................... G10L 25/78
(Continued)

FOREIGN PATENT DOCUMENTS

| JP | 2006-295669 A | 10/2006 |
| JP | 2015-211267 A | 11/2015 |

(Continued)

OTHER PUBLICATIONS

Extended European Search Report received in corresponding European Application No. 19917870.8 dated Feb. 6, 2023.
(Continued)

*Primary Examiner* — Lun-See Lao
(74) *Attorney, Agent, or Firm* — Mattingly & Malur, PC

(57) ABSTRACT

The present invention relates to a head-mountable information processing apparatus allowing a user to hear a desired sound even if ambient sound unnecessary for the user is present. An audio input interface includes sound microphones worn in the vicinity of the user's ear, collects the ambient sound that occurs outside the head-mountable information processing apparatus, and converts the ambient sound into an input audio signal. An audio output interface, including headphones, converts a generated output audio signal for output, and emits the audio output toward the user. Based on a volume level of the input audio signal and a volume level of the output audio signal, a controller determines whether or not a state in which the ambient sound is preventing the audio for output from being heard is occurring, and based on a determination result, the controller controls a sound emission operation of the audio output interface.

15 Claims, 12 Drawing Sheets

(51) Int. Cl.
  *A61B 5/021* (2006.01)
  *A61B 5/024* (2006.01)
  *G01C 17/28* (2006.01)
  *G01P 3/00* (2006.01)
  *G06F 3/01* (2006.01)
  *G10L 15/22* (2006.01)
  *G10L 25/51* (2013.01)
  *H04R 1/10* (2006.01)
  *H04R 3/00* (2006.01)

(52) U.S. Cl.
  CPC ............ *A61B 5/6803* (2013.01); *G06F 3/012* (2013.01); *G06F 3/013* (2013.01); *G10L 15/22* (2013.01); *G10L 25/51* (2013.01); *H04R 1/1008* (2013.01); *H04R 1/1041* (2013.01); *H04R 3/00* (2013.01); *G01C 17/28* (2013.01); *G01P 3/00* (2013.01); *G10L 2015/223* (2013.01); *H04R 2430/01* (2013.01); *H04R 2499/15* (2013.01)

(58) Field of Classification Search
  CPC ..... G10L 25/78; H04R 1/1008; H04R 1/1041; H04R 1/1016; H04R 1/1091; H04R 2430/01; H04R 2430/21; H04R 2499/15; H04R 3/00; H04R 3/005; H04M 1/72403; H04M 1/72412; H04M 1/72457
  USPC ................................ 381/56–58, 74, 104–107
  See application file for complete search history.

(56) References Cited

U.S. PATENT DOCUMENTS

| | | |
|---|---|---|
| 2015/0130702 A1* | 5/2015 | Kato ...................... G06F 3/005 345/156 |
| 2015/0312674 A1 | 10/2015 | Fukui |
| 2015/0334292 A1* | 11/2015 | Tartz ...................... H04N 23/61 348/222.1 |
| 2016/0093207 A1 | 3/2016 | Di Censo et al. |
| 2018/0167753 A1 | 6/2018 | Yen et al. |
| 2018/0260187 A1 | 9/2018 | Yasuda |
| 2018/0286424 A1 | 10/2018 | Fadell et al. |
| 2018/0302738 A1 | 10/2018 | Di Censo et al. |
| 2018/0324539 A1 | 11/2018 | Lovitt |

FOREIGN PATENT DOCUMENTS

| | | |
|---|---|---|
| JP | 2016-172038 A | 9/2016 |
| JP | 2016-198378 A | 12/2016 |
| JP | 2017-064429 A | 4/2017 |
| JP | 2017-069687 A | 4/2017 |
| JP | 2017-086529 A | 5/2017 |
| JP | 2017-086530 A | 5/2017 |
| JP | 2017-202047 A | 11/2017 |

OTHER PUBLICATIONS

International Search Report of PCT/JP2019/008457 dated May 21, 2019.
Partial Supplementary European Search Report received in corresponding European Application No. 19917870.8 dated Sep. 28, 2022.

* cited by examiner

FIG. 11

| No  | SITUATIONS WHERE USER-UNSUITABLE STATE OCCURS |
|-----|-----------------------------------------------|
| (1) | USER IS PAYING ATTENTION TO VR OR AR INFORMATION |
| (2) | USER IS MAKING RAPID EYE MOVEMENT |
| (3) | USER IS NOT CLEARLY CONSCIOUS |
| (4) | USER'S HEAD IS MOVING SIGNIFICANTLY |
| (5) | USER'S PHYSICAL CONDITION CHANGES |
| (6) | USER IS HAVING A CONVERSATION WITH ANOTHER PERSON |
| (7) | APPROACHING OBJECT IS PRESENT IN USER'S SURROUNDINGS |

HEAD-MOUNTABLE INFORMATION PROCESSING APPARATUS

TECHNICAL FIELD

The present invention relates to a head-mountable information processing apparatus used by being worn on a user's head and having functions for viewing images and hearing audio.

BACKGROUND ART

Patent Document 1 discloses a mobile terminal comprising a determiner configured to determine whether or not ambient sound should be output to an earphone based on an audio signal input from at least one microphone, and an audio output controller configured to output the audio signal input from the at least one microphone to the earphone if it is determined that the ambient sound should be output to the earphone.

RELATED ART DOCUMENTS

Patent Documents

Patent Document 1: Japanese Laid-Open Patent Publication No. 2015-211267

SUMMARY OF THE INVENTION

Problems to be Solved by the Invention

In general, a head-mountable information processing apparatus is capable of displaying real space or virtual space (virtual object) on a display worn on a user's head. In recent years, it has become possible for such a head-mountable information processing apparatus to seamlessly integrate real and virtual worlds in real time to provide the user an experience in which the virtual object seems to be present in the current scene. Conventionally, in the head-mountable information processing apparatus used by allowing an audio output interface such as a pair of headphones along with a display to be worn on the user's head, the audio signal output from inside the head-mountable information processing apparatus is converted into audio in the audio output interface and is emitted to transmit the audio signal to the user.

Among the audio output interfaces, air conduction headphones which listen to air-conducted sound transmitted by vibration of air are worn so as to be in contact with a surface of the ears, and in particular, open-ear headphones may be worn without completely covering the ears. This may allow ambient sound to enter the ears via the surroundings of the headphones, and be picked up and heard. In addition, bone conduction headphones which listen to bone-conducted sound transmitted by vibration of the bone are worn without completely covering the ears. This allows the ambient sound to enter the ears and be heard as is.

Ambient sounds include sounds that are necessary for the user (such as being called by another person or a siren of an emergency vehicle), and sounds that are unnecessary for the user (such as running sounds of trains and cars, conversations between other people, loud noise such as fireworks or thunder, or noise from strong winds and heavy rain). To deal with such an ambient sound, Patent Document 1 discloses a method to determine whether or not the ambient sound collected by a microphone is highly necessary for the user in a state in which earphones are worn on the ears, and to allow the user to hear the highly necessary ambient sound from the earphones.

Although Patent Document 1 discloses the method for hearing the ambient sound highly necessary for the user, the document fails to suggest a method or the like for dealing with the ambient sound unnecessary for the user, and there is a problem in which the ambient sound unnecessary for the user prevents the user from seeing or hearing the audio signals emitted from inside the head-mountable information processing apparatus. In particular, in a case where the audio signal emitted from inside the head-mountable information processing apparatus is expressed in words, there is a problem in which the unnecessary ambient sound prevents the user from properly hearing audio that assists the user such as a calling or a warning consisting of words, whereby the user may miss hearing the audio.

The present invention has been made in view of the problems described above, and provides a head-mountable information processing apparatus that allows the user to reliably hear a desired sound even if the ambient sound unnecessary for the user is present.

Means for Solving the Problems

The following briefly describes an overview of a representative invention among the inventions disclosed in the present application.

The head-mountable information processing apparatus according to one embodiment is an apparatus worn on a user's head and having a function for viewing images or hearing audio. The head-mountable information processing apparatus is equipped with an audio input interface, an audio output interface, and a controller configured to control an operation of the head-mountable information processing apparatus. The audio input interface is worn in the vicinity of the user's ear, collects ambient sound that occurs outside the head-mountable information processing apparatus and enters the ear, and converts the ambient sound into an input audio signal. The audio output interface generates an output audio signal, converts the generated output audio signal into an audio for output, and emits the audio for output toward the user. Based on a volume level of the input audio signal from the audio input interface and a volume level of the output audio signal from the audio output interface, the controller determines whether or not a state in which the ambient sound is preventing the audio for output from being heard is occurring, and based on a determination result, the controller controls a sound emission operation of the audio output interface.

In addition, the head-mountable information processing apparatus according to one embodiment comprises a display, an audio output interface, a sensor device, a user state determiner, and a controller configured to control an operation of the head-mountable information processing apparatus. The display displays predetermined information including virtual space information or real space information to the user. The audio output interface generates an output audio signal, converts the generated output audio signal into an audio for output, and emits the audio for output toward the user. The sensor device detects a state of the user or a state of the user's surroundings. Based on a detection result of the sensor device, the user state determiner determines whether or not the state of the user or the state of the user's surroundings is a state suitable for hearing the audio for output. Based on a determination result of the user state determiner, if it is determined that the state is suitable for hearing the audio for output, the controller causes the audio output interface to perform sound emission, and if it is determined that the state is not suitable for hearing the audio for output, the controller instructs the audio output interface to interrupt sound emission.

Effects of the Invention

The head-mountable information processing apparatus of the present invention allows the user to reliably hear a desired sound even if the ambient sound unnecessary for the user is present.

Problems, configurations and effects other than those described above will be apparent from the following description of the embodiments.

BRIEF DESCRIPTION OF THE DRAWINGS

FIG. 11 is a table describing examples of user-unsuitable states in FIG. 10.

DETAILED DESCRIPTION OF PREFERRED EMBODIMENTS

Hereinafter, embodiments of the present invention will be described in detail with reference to the drawings. Note that, in all of the drawings that describe the embodiments, the same members are generally denoted by the same reference signs, and redundant descriptions thereof will be omitted as appropriate.

First Embodiment

Overview of Head-Mountable Information Processing Apparatus

Figure 1:
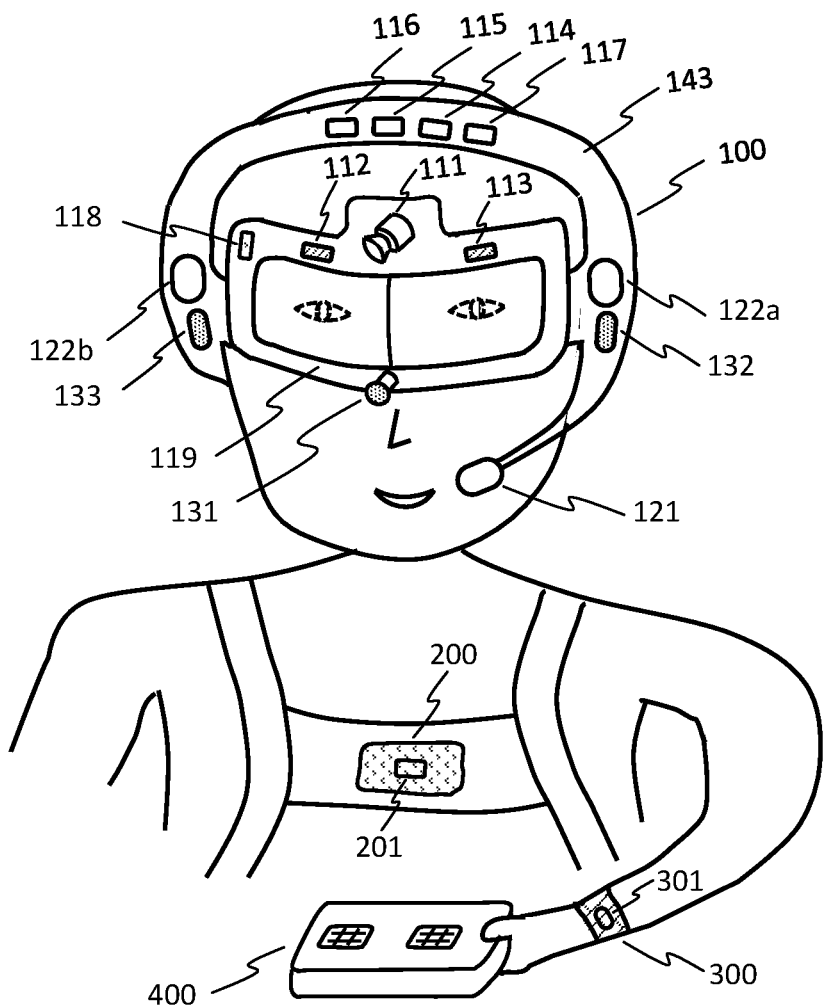
FIG. 1 is a schematic view showing an example of an external configuration of a head-mountable information processing apparatus according to a first embodiment of the present invention.

FIG. 1 is a schematic view showing an example of an external configuration of a head-mountable information processing apparatus according to a first embodiment of the present invention. The head-mountable information processing apparatus of FIG. 1 comprises a main body (head-mountable display) 100 of the head-mountable information processing apparatus worn on a user's head, a chest-mounting type wearable terminal 200 worn on a user's chest or a wristband type wearable terminal 300 worn on a user's arm, and an input controller 400.

The main body 100 comprises a camera 111, and a sensor device configured to detect a state of the user or a state of the user's surroundings. The sensor device includes a right eye gaze sensor 112, a left eye gaze sensor 113, an acceleration sensor 114, a gyro sensor 115, a geomagnetic sensor 116, a temperature/humidity sensor 117, a peripheral object detection sensor 118, a vocal sound microphone 121, first to third peripheral sound microphones 131 to 133 or the like. The main body 100 uses the camera 111 to capture an image in front of the user, and uses the sensor device to detect the user's eye gaze, movement of the user's head, temperature/humidity in the user's surroundings, presence of objects in the user's surroundings or the like.

In addition, the main body 100 comprises a display 119. The display 119 is installed in front of both eyes, and displays, for example, predetermined information such as virtual space information or real space information captured by the camera 111 to the user. The vocal sound microphone 121 collects a vocal sound from the user, and converts the sound into an audio signal. The first to third peripheral sound microphones 131 to 133 configure the audio input interface. The audio input interface is worn in the vicinity of the user's ear, collects ambient sound that occurs outside the head-mountable information processing apparatus and enters the ear, and converts the ambient sound into an input audio signal. The first peripheral sound microphone 131 is provided in, for example, a center portion of the head-mountable information processing apparatus, and collects sound spoken by another person or the like toward the user. The second and third peripheral sound microphones 132 and 133 are provided so as to be in contact with the user's left and right ears, and collect the ambient sounds that enter the user's ears from the outside.

In addition, the main body 100 comprises a pair of headphones 122 (122a and 122b) respectively worn on the user's left and right ears. The pair of headphones 122a and 122b configures the audio output interface, respectively converts the left and right output audio signals generated inside the head-mountable information processing apparatus into left and right audios for output, and emits the left and right audios for output toward the user. Note that, when the user hears sound from the audio output interface, there may be a case where the user hears air-conducted sound having entered the ear and being transmitted by vibration of air, and there may be a case where the user hears bone-conducted sound transmitted by bone vibration without passing through the ears. In this regard, the pair of headphones 122 may be of an air-conducted sound type, or may be of a bone-conducted sound (bone conduction) type.

The chest-mounting type wearable terminal 200 comprises a heart rate sensor 201 which is a sensor device, and detects a heart rate which is the number of times the heart beats within a certain period of time. The wristband type wearable terminal 300 comprises a blood pressure sensor 301 which is a sensor device, and detects the user's blood pressure. Note that the wristband type wearable terminal 300 may comprise a pulse sensor, and may detect a pulse rate which is the number of arterial beats. The input controller 400 is used by the user to perform various input operations. The chest-mounting type wearable terminal 200, the wristband type wearable terminal 300 and the input controller 400 transmit and receive information to and from the main body 100 via short-range wireless communication. At this time, information may be transmitted and received not only via wireless communication but also via wired communication.

As described above, in the head-mountable information processing apparatus worn in close contact with the user, the ambient sound that enters the ear can be detected by the audio input interface such as the second and third peripheral sound microphones 132 and 133 in the main body 100. In addition, the state of the user (such as mental and physical states and body movement) and the state of the user's surroundings can be detected by various sensor devices in the main body 100 and the wearable terminals 200 and 300. In addition, based on a user input operation via the input controller 400, the display 119 provided in front of both eyes of the user in the main body 100 can display predetermined information including the real space information or the virtual space information.

Figure 2:
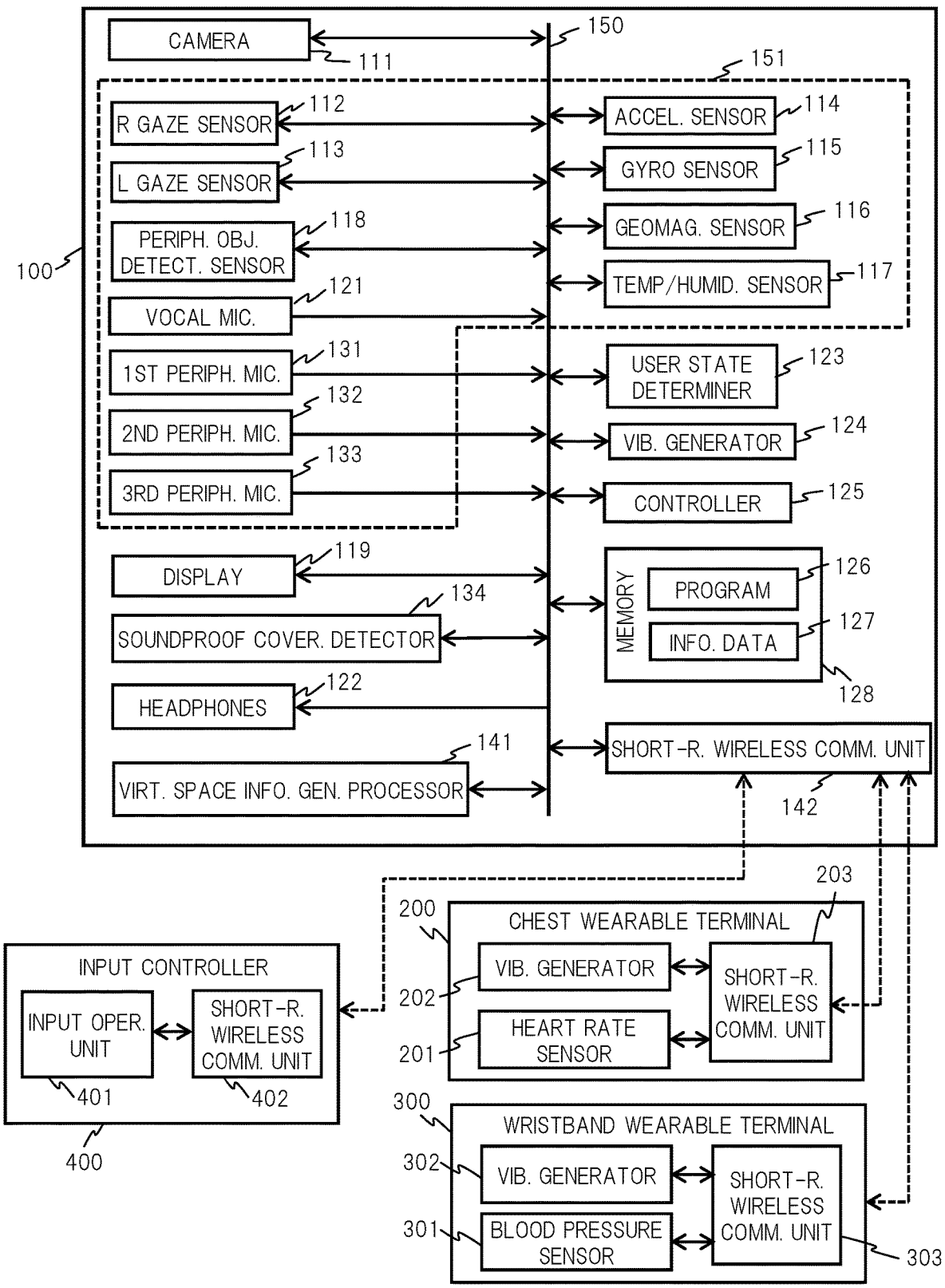
FIG. 2 is a block diagram showing a schematic configuration example of the head-mountable information processing apparatus of FIG. 1.

FIG. 2 is a block diagram showing a schematic configuration example of the head-mountable information processing apparatus of FIG. 1. In FIG. 2, the main body 100 comprises the camera 111, various sensor devices 151 (112 to 118, 121, 131 to 133), the display 119 and the pair of headphones 122 described with reference to FIG. 1. In addition, the main body 100 further comprises a user state determiner 123, a vibration generator 124, a controller 125, a memory 128, a soundproof ear-covering detector 134, a virtual space information generation processor 141, and a short-range wireless communication unit 142. These components are connected to one another via a bus 150.

The camera 111 is installed on a front surface of the main body 100, and captures a scenery in front of the user. The captured image is displayed on the display 119 as an image of the real space. The right eye gaze sensor 112 and the left eye gaze sensor 113 respectively detect the gazes of the right eye and the left eye. A technique for detecting the user's eye gaze is commonly known as eye tracking. For example, in eye tracking using corneal reflection, infrared LED (Light Emitting Diode) is irradiated on the face and is captured by an infrared camera, a position on a cornea of the reflected light (corneal reflection) generated by irradiation of the infrared LED is set as a reference point, and the eye gaze is detected based on a position of a pupil with respect to the position of the corneal reflection.

The acceleration sensor 114 is a sensor configured to detect acceleration which is a change in velocity per second, and detects movement, vibration, impact or the like. The gyro sensor 115 is a sensor configured to detect an angular velocity in a rotation direction, and a state of vertical, horizontal or diagonal postures. The geomagnetic sensor 116 is a sensor configured to detect magnetic force of the earth, and detects a direction in which the main body 100 is facing. Therefore, by using the gyro sensor 115 or the geomagnetic sensor 116, and in some cases the acceleration sensor 114 in combination, movement of the head of the user wearing the main body 100 can be detected. In particular, by using the 3-axis type geomagnetic sensor 116 configured to detect a geomagnetic field in a vertical direction in addition to a front-back direction and a left-right direction to detect the geomagnetic field change with respect to the movement of the head, it is possible to detect the movement of the head with higher accuracy.

The temperature/humidity sensor 117 is a sensor configured to detect temperature and humidity of the user's surroundings. The peripheral object detection sensor 118 is a sensor configured to emit radio waves, light waves, ultrasonic waves or the like and detect the reflected wave from the target object to detect a distance from the target object, direction of the target object, or a relative velocity. The peripheral object detection sensor 118 is worn on the user's head to detect a distance to an object present in the user's surroundings, a relative velocity of the object, and a direction in which the object is present.

At the time of emitting the output audio signal generated inside the head-mountable information processing apparatus as an audio for output via the pair of headphones 122 (audio output interface), based on detection results of the various sensor devices 151, the user state determiner 123 determines whether or not the state of the user or the state of the user's surroundings is in a state suitable for hearing the audio for output. The user state determiner 123 determines that the state is not suitable for hearing the audio for output in various predetermined cases such as if the user is considered to be paying attention to the virtual space information or the real space information on the display 119, as will be described in detail below with reference to FIG. 10 and thereafter.

The controller 125 is constituted by, for example, a CPU (Central Processing Unit) or the like, and executes a program 126 such as an OS (Operating System) or an application for operation control stored in the memory 128 to control each of the components and an operation of the entire head-mountable information processing apparatus. Based on a volume level of the input audio signal from the audio input interface (second and third peripheral sound microphones 132 and 133) and a volume level of the output audio signal from the audio output interface (such as headphones 122), the controller 125 determines whether or not a state in which the ambient sound is preventing the audio for output from being heard is occurring, and based on a determination result, the controller 125 controls a sound emission operation of the audio output interface, as will be described in detail below.

The memory 128 is a flash memory, a workstation RAM or the like. The memory 128 stores the program 126 such as the OS or the application for operation control used by the controller 125. In addition, the memory 128 stores various information data 127 such as data of the output audio signal generated in the main body 100, the virtual space information generated in the virtual space information generation processor 141, and information from the wearable terminals 200 and 300. Examples of data of the output audio signal generated in the main body 100 include data of a voice assistant that responds to a user's request via voice interaction with the user by audio such as calling to the user, guidance, information transmission, warning or the like.

The display 119 is constituted by a liquid crystal panel or the like, displays the real space information or the virtual space information through an image, and also displays display contents such as user notification information for the user and an operation state on the screen. The display 119 may display, for example, a notification to notify the user of the fact that emission of the output audio signal is starting, is being interrupted, or is resuming. In this manner, when sound emission is interrupted or resumed, the user can recognize that sound emission being interrupted or resuming was not caused by a malfunction but by a normal control operation.

The vibration generator 124 generates a vibration in response to an instruction from the controller 125, and converts, for example, the notification information for the user generated in the main body 100 into a vibration. The vibration generator 124 generates a vibration while being worn in close contact with the user's head to provide a highly recognizable notification to the user. For example, in a case where a capturing range of the camera 111 includes the ears, based on an image thereof, the soundproof ear-covering detector 134 detects whether or not the user's ears are covered with his/her hands or the like and the ambient sound is prevented from entering the ears. Note that it is also possible to detect whether or not the ambient sound is soundproofed by a magnitude of the ambient sound entering the second and third peripheral sound microphones 132 and 133.

The virtual space information generation processor 141 generates the virtual space information in which a virtual space that differs from the real space is expressed by an image or a sound. The short-range wireless communication unit 142 is a communication interface configured to perform short-range wireless communication between each of the chest-mounting type wearable terminal 200, the wristband type wearable terminal 300 and the input controller 400 present in a range where short-range wireless communication is possible. For example, the short-range wireless communication unit 142 receives detection information from the sensors mounted on each of the wearable terminals 200 and 300, transmits control information for controlling the vibration generator mounted on each of the wearable terminals 200 and 300, transmits and receives input operation information to and from the input controller 400, or the like.

Note that the short-range wireless communication unit 142 is typically an electronic tag. However, it is not limited to this, and may be a component capable of at least performing wireless communication when the main body 100 is close to the chest-mounting type wearable terminal 200, the wristband type wearable terminal 300 and the input controller 400. Examples of such a component include Bluetooth (registered trademark), IrDA (Infrared Data Association), Zigbee (registered trademark), HomeRF (Home Radio Frequency; registered trademark), and wireless LAN (IEEE802.11a, IEEE802.11b, IEEE802.11g).

The chest-mounting type wearable terminal 200 has the heart rate sensor 201 which is a sensor device, a vibration generator 202, and a short-range wireless communication unit 203. The heart rate sensor 201 is worn in close contact with the user's chest, and accurately detects the user's heart rate. The short-range wireless communication unit 203 transmits information of the detected heart rate to the main body 100 via short-range wireless communication. The vibration generator 202 generates a vibration in response to a control input, and is worn in close contact with the user's chest to reliably transmit the generated vibration to the user.

The wristband type wearable terminal 300 has the blood pressure sensor 301 which is a sensor device, a vibration generator 302, and a short-range wireless communication unit 303. The blood pressure sensor 301 is worn around the user's arm to accurately detect the user's blood pressure. The short-range wireless communication unit 303 transmits information of the detected blood pressure to the main body 100 via short-range wireless communication. The vibration generator 302 generates a vibration in response to an input, and is worn around the user's arm to reliably transmit the generated vibration to the user.

Here, the main body 100 receives information on the heart rate from the heart rate sensor 201 and information on the blood pressure from the blood pressure sensor 301 via the short-range wireless communication unit 142. Based on the information on the heart rate or the information on the blood pressure, the user state determiner 123 can determine whether or not the state of the user (physical/mental state) is a state suitable for hearing the audio for output. In addition, the notification information for the user transmitted from the main body 100 is transmitted to the vibration generators 202 and 302 of the respective wearable terminals 200 and 300 via the short-range wireless communication units 142, 203 and 303. The vibration generators 202 and 302 convert the notification information into vibrations to inform the user of the notification information.

Note that the vibration generator 124 of the main body 100 and the vibration generators 202 and 302 of the respective wearable terminals 200 and 300 may generate vibrations to notify the user of the fact that, for example, emission of the output audio signal is starting, is being interrupted, or is resuming. In this manner, the user can strongly recognize that, for example, sound emission has been interrupted or has resumed. In addition, the main body 100 may emit audio from the pair of headphones 122 informing that sound emission has been interrupted or has resumed to notify and inform the user.

The input controller 400 has an input operation unit 401 and a short-range wireless communication unit 402. The input operation unit 401 is an input means such as a keyboard or a key button, and allows the user to set and input information as desired. In addition, the input operation unit 401 may be an input means of a touch pad method such as a capacitive type touch pad. Information input by the input operation unit 401 is transmitted to the main body 100 via the short-range wireless communication unit 402. Here, wireless communication is used to improve usability. However, it goes without saying that wired communication may also be used.

Details of the Controller

Figure 3:
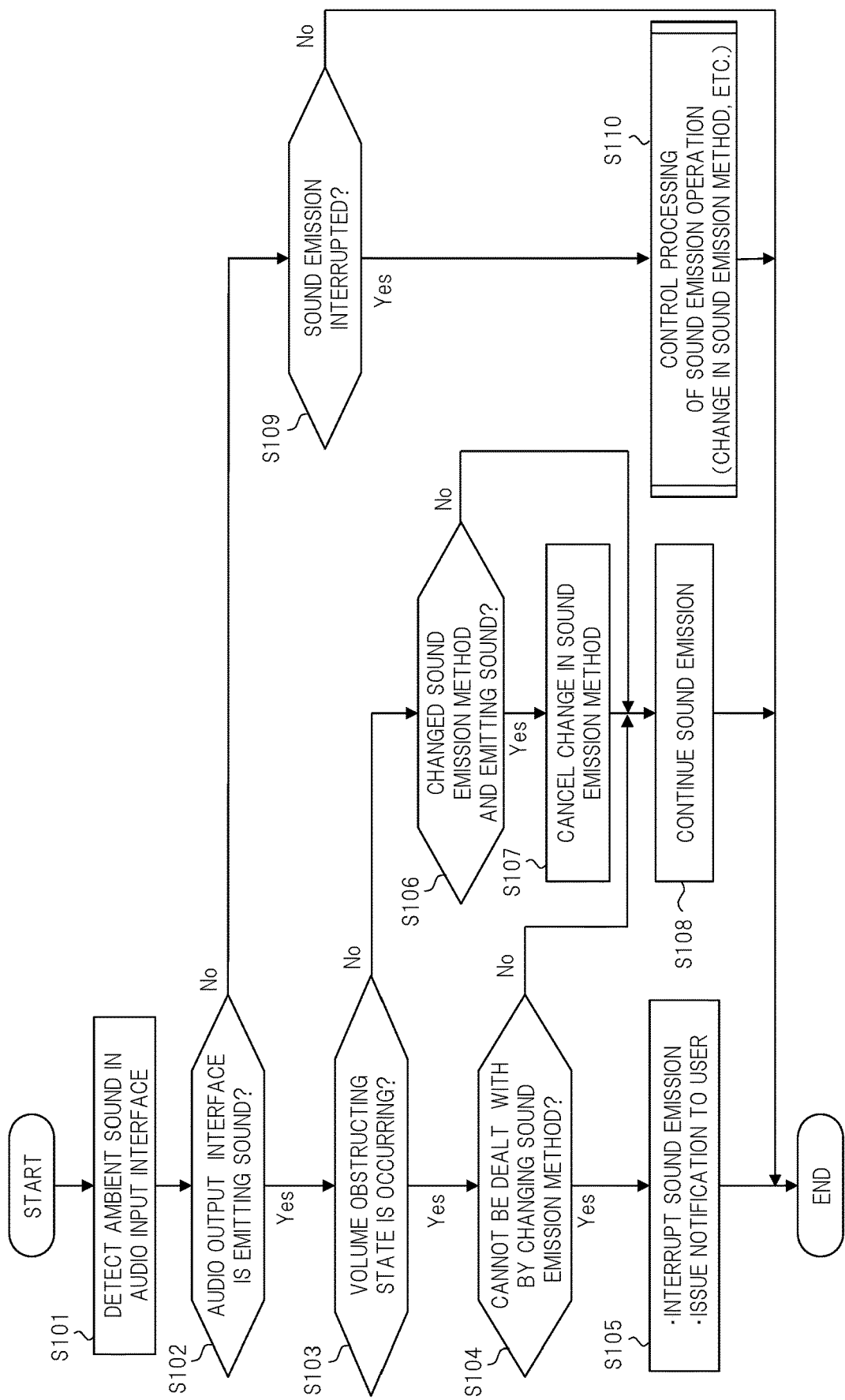
FIG. 3 is a flowchart showing an example of detailed processing contents in the controller of FIG. 2.
Figure 4:
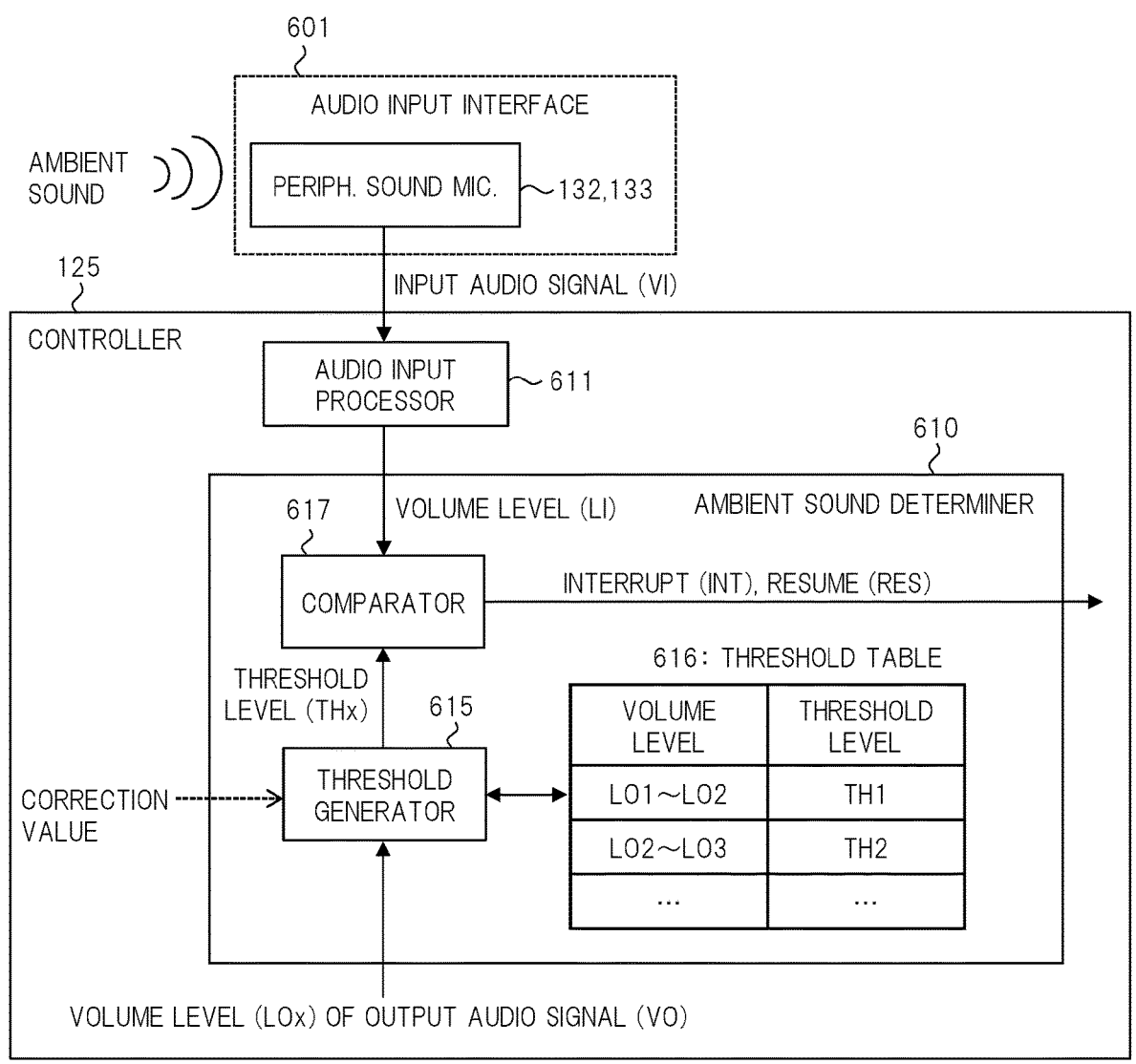
FIG. 4 is a block diagram showing a configuration example of a main portion around the controller with respect to an audio input in FIG. 2.

FIG. 3 is a flowchart showing an example of detailed processing contents in the controller of FIG. 2. FIG. 4 is a block diagram showing a configuration example of a main portion around the controller with respect to an audio input in FIG. 2. The controller 125 of FIG. 2 repeatedly executes the flow shown in FIG. 3 at a predetermined control cycle. In FIG. 3, the controller 125 uses the audio input interface (second and third peripheral sound microphones 132 and 133) to detect the ambient sound (step S101). Next, the controller 125 determines whether or not the audio output interface (such as headphones 122) is emitting the audio for output (step S102). If it is determined that the audio for output is being emitted in step S102, based on a volume level of the ambient sound detected in step S101, the controller 125 determines whether or not the state in which the ambient sound is preventing the audio for output from being heard is occurring in terms of the volume level (step S103). In the present specification, this state in which the ambient sound is preventing the audio for output from being heard in terms of the volume level is also referred to as a volume obstructing state.

If it is determined that the volume obstructing state is occurring in step S103, the controller 125 determines whether or not the issue cannot be dealt with by changing a sound emission method (step S104). Changing the sound emission method includes, for example, a process to change frequency characteristics of the output audio signal, as will be described in detail below. If it is determined that the issue cannot be dealt with by changing the sound emission method in step S104, the controller 125 instructs the audio output interface to interrupt sound emission (step S105). Further, in step S105, the controller 125 uses a notice display on the display 119, a tactile vibration by the vibration generators 124, 202 and 302, or a vocal sound by the audio output interface (headphones 122) to notify the user of the fact that sound emission is being interrupted, and ends the process.

If it is determined that the volume obstructing state is not occurring in step S103, the controller 125 determines whether or not the audio output interface has changed the sound emission method and is emitting sound (step S106). If it is determined that the sound emission method has changed and sound is being emitted in step S106, the controller 125 cancels the change in the sound emission method in step S107 (that is, returns to the default sound emission method), then continues sound emission by the audio output interface in step S108, and ends the process. On the other hand, if it is determined that the sound is not being emitted with the changed sound emission method in step S106 (that is, sound is being emitted by the default sound emission method), the controller 125 continues sound emission by the audio output interface as is, and ends the process (step S108). Note that the controller 125 continues sound emission by the audio output interface even in a case where the issue can be dealt with by changing the sound emission method in step S104 (step S108).

If it is determined that the audio for output is not being emitted in step S102, the controller 125 determines whether or not the audio output interface is interrupting sound emission (step S109). If it is determined that sound emission is interrupted in step S109, the controller 125 executes a control processing of the sound emission operation in step S110, and ends the process, as will be described in detail below. The control processing of the sound emission operation includes sound emission operation changing the sound emission method or the like. On the other hand, if it is determined that sound emission is not interrupted in step S109, the controller 125 ends the process.

FIG. 4 shows a configuration example around the controller 125 related to step S103 of FIG. 3 (that is, determining whether or not the volume obstructing state is occurring). FIG. 4 shows the controller 125 and an audio input interface 601. The audio input interface 601 comprises the second and third peripheral sound microphones 132 and 133 each configured to collect the ambient sound that enters the ear and convert the ambient sound into an input audio signal (VI). On the other hand, the controller 125 comprises an ambient sound determiner 610 and an audio input processor 611. The audio input processor 611 receives, for example, the input audio signal (VI) from the audio input interface 601, and detects its volume level (LI).

The ambient sound determiner 610 comprises a threshold generator 615, a threshold table 616, and a comparator 617. The threshold table 616 has a predefined correspondence between each range of the volume level (LOx) of the output audio signal (VO) from the audio output interface and a threshold level representing a relative ambient sound tolerance value for each range. The threshold generator 615 receives the volume level (LOx) of the output audio signal (VO) recognized in advance inside the apparatus, and generates a threshold level (THx) corresponding to the volume level (LOx) based on the threshold table 616.

The comparator 617 compares the volume level (LI) of the input audio signal (VI) from the audio input processor 611 and the threshold level (THx) from the threshold generator 615 to determine whether or not to instruct the audio output interface to interrupt sound emission. In other words, the comparator 617 determines whether or not the state in which the ambient sound corresponding to the input audio signal (VI) is preventing the audio for output corresponding to the output audio signal (VO) from being heard is occurring. That is, the comparator 617 determines whether or not the volume obstructing state is occurring.

Specifically, if the volume level (LI) of the input audio signal (VI) is greater than or equal to the threshold level (THx), the comparator 617 determines that the state in which the ambient sound is preventing the audio for output from being heard is occurring (state in which the volume obstructing state is occurring), and issues a sound emission interrupt instruction (INT) to the audio output interface. In addition, if the volume level (LI) of the input audio signal (VI) becomes less than the threshold level (THx) while the audio output interface is interrupting sound emission (that is, during control processing of the sound emission operation in step S110 of FIG. 3), the comparator 617 determines that a state in which the ambient sound is not preventing the audio for output from being heard is occurring, and issues a sound emission resume instruction (RES) to the audio output interface. In other words, the comparator 617 determines that the volume obstructing state is resolved, and issues the sound emission resume instruction (RES) to the audio output interface.

Here, individual differences can occur in the volume level of the ambient sound which the user finds to be distracting when listening to the audio for output. Therefore, the threshold generator 615 is capable of adding a correction to the threshold level (THx) according to the user settings. Here, the threshold level (THx) is generated by using the threshold table 616. However, it is also possible to generate the threshold level (THx) using, for example, a predetermined calculation formula or the like.

In addition, a relative comparison between the volume level (LI) of the input audio signal (VI) and the volume level (LOx) of the output audio signal (VO) was used here. However, in some cases, an absolute comparison of the volume level (LI) of the input audio signal (VI) may be used, or a combination the relative comparison and the absolute comparison may be used. For example, in a case where the ambient sound is significantly large, the state in which the ambient sound is preventing the audio for output from being heard is occurring can be detected by an absolute comparison using only the volume level (LI) of the input audio signal (VI).

Further, the ambient sound determiner 610 and the audio input processor 611 may be provided in the user state determiner 123 of FIG. 2 configured to determine whether or not the state of the user or the state of the user's surroundings is a state suitable for hearing the audio for output. That is, FIG. 2 shows the controller 125 and the user state determiner 123 separately mainly from the viewpoint of functions for the sake of convenience. However, the controller 125 can include the function of the user state determiner 123. In addition, from the viewpoint of hardware, the user state determiner 123 can be achieved by a program processing by, for example, a CPU, and in this case, the controller 125 can include the user state determiner 123.

Control Processing [1] of Sound Emission Operation

Figure 5:
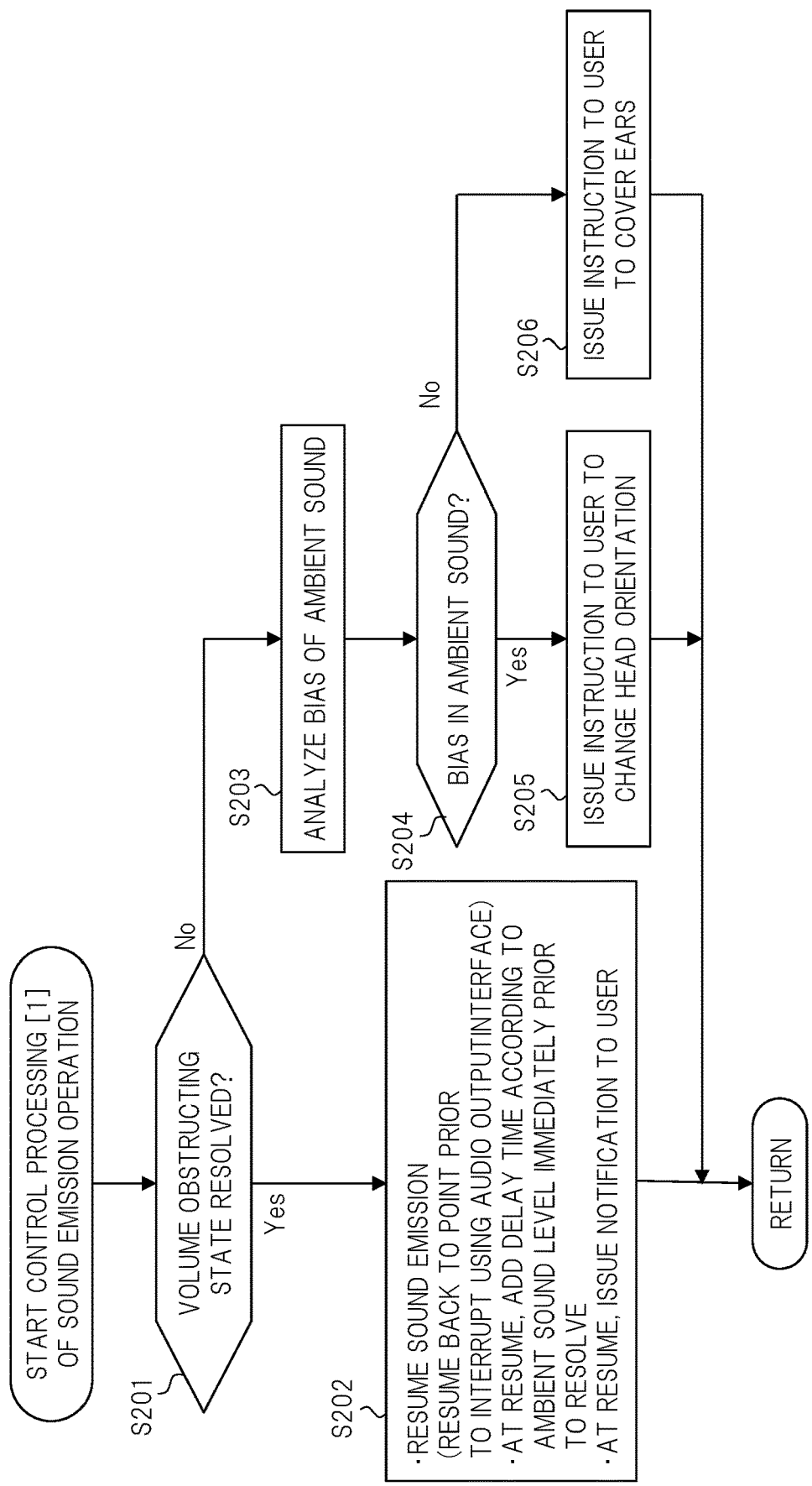
FIG. 5 is a flowchart showing an example of detailed processing contents of a control processing of a sound emission operation in FIG. 3.
Figure 6:
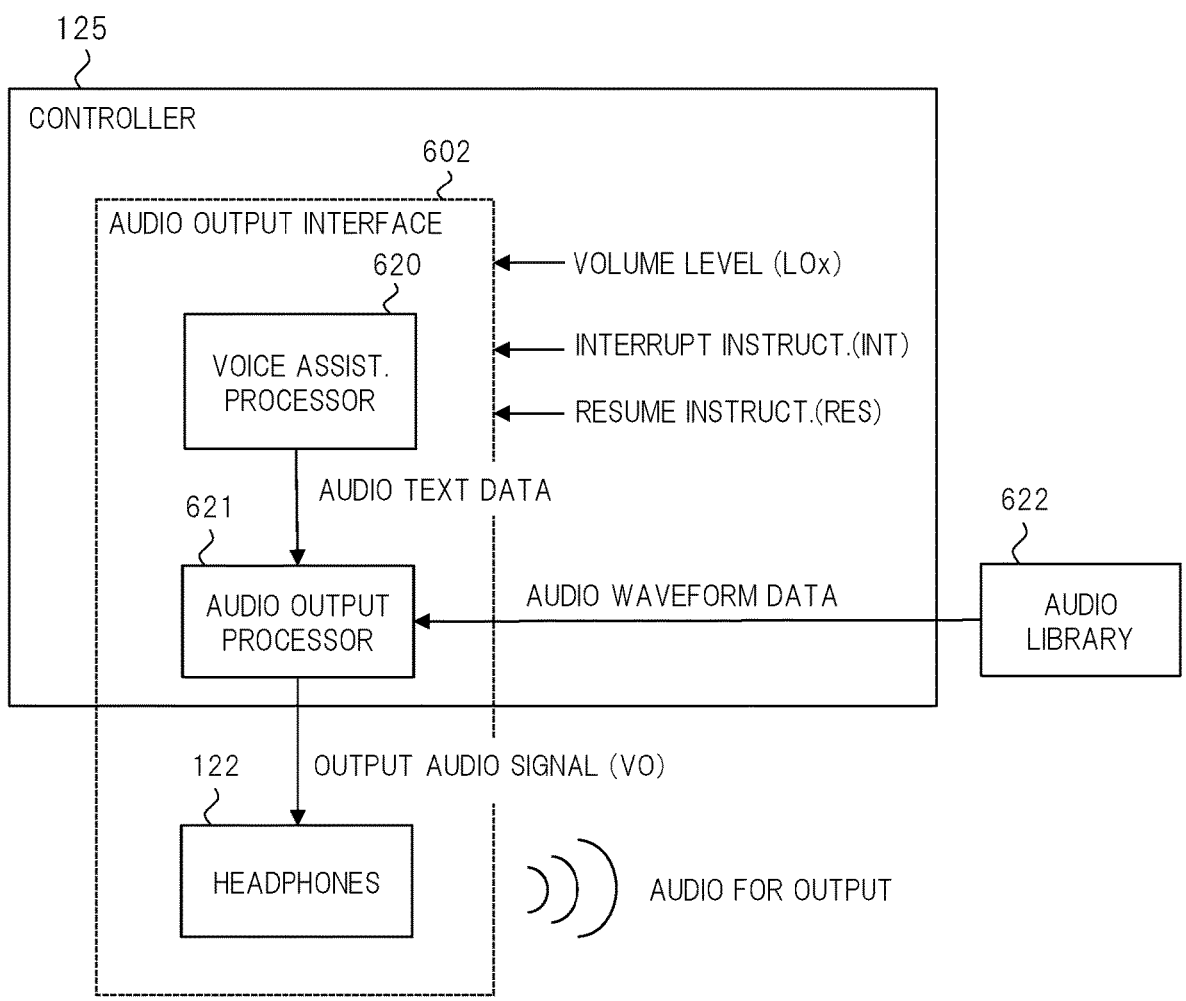
FIG. 6 is a block diagram showing a configuration example of the main portion around the controller with respect to an audio output in FIG. 2.

FIG. 5 is a flowchart showing an example of detailed processing contents of the control processing of the sound emission operation in FIG. 3. FIG. 6 is a block diagram showing a configuration example of the main portion around the controller with respect to the audio output in FIG. 2. FIG. 5 shows the processing contents of the control processing (step S110) of the sound emission operation performed while sound emission is interrupted in FIG. 3, and shows one example of the processing contents of a control processing [1].

In FIG. 5, the controller 125 determines whether or not the volume obstructing state (state in which the ambient sound is preventing the audio for output from being heard) as described for step S103 of FIG. 3 and FIG. 4 is resolved (step S201). As described with reference to FIG. 4, if it is determined that the volume obstructing state is resolved in step S201, the controller 125 (specifically, the ambient sound determiner 610) issues the resume instruction (RES) to instruct the audio output interface to resume sound emission. In response to the resume instruction (RES), the audio output interface resumes sound emission by going back to a point prior to interrupt (step S202).

In step S202, at the time of resuming sound emission, the controller 125 adds the delay time according to the volume level (LI) of the ambient sound (input audio signal (VI)) immediately prior to the volume obstructing state being resolved, as will be described in detail below with reference to FIG. 7. Specifically, for example, after a predetermined period according to the volume level (LI) of the input audio signal (VI) immediately prior to the state in which the ambient sound is not preventing the audio for output from being heard is occurring has passed, the controller 125 issues the resume instruction (RES) to the audio output interface. Further, in step S202, the controller 125 uses the notice display on the display 119, the tactile vibration by the vibration generators 124, 202 and 302, or the vocal sound by the audio output interface (headphones 122) to notify the user of the fact that sound emission is resuming, and ends the process. In the subsequent control cycle, the sound emission operation continues in the order of steps S101, S102, S103, S106 and S108 of FIG. 3.

On the other hand, in step S201, if it is determined that the volume obstructing state is still occurring, the controller 125 analyzes a bias of the ambient sound (step S203), and determines whether or not there is a bias in the ambient sound (step S204). Specifically, for example, the audio input processor 611 in the controller 125 in FIG. 4 determines whether or not there is a bias of a predetermined reference value or more in the volume levels (LI) of the left and right input audio signals (VI) from the second and third peripheral sound microphones 132 and 133.

If it is determined that there is a bias in the ambient sound in step S204, the controller 125 uses the display 119 to instruct the user to change an orientation of his/her head, and ends the process (step S205). Then, as the user changes the orientation of his/her head, the bias of the ambient sound decreases. As a result, when step S201 of FIG. 4 is reached via the flow of FIG. 3 in a subsequent control cycle, if the volume obstructing state is resolved, sound emission is resumed in step S202.

On the other hand, there may be a case where the volume obstructing state is not resolved even if the user changes the orientation of his/her head to minimize the bias of the ambient sound. In this case, the controller 125 proceeds from step S204 to step S206, and in step S206, uses the display 119 to issue an instruction to the user to cover his/her ears with his/her hands, and ends the process. Thereafter, in a case where, for example, the user wishes to hear the audio for output, the user covers his/her ears so as to include the second and third peripheral sound microphones 132 and 133. As a result, normally, when step S201 of FIG. 4 is reached via the flow of FIG. 3 in the subsequent control cycle, the volume obstructing state is resolved, and sound emission is resumed in step S202.

Here, the controller 125 indirectly determines whether or not the user has covered his/her ears based on detection results of the second and third peripheral sound microphones 132 and 133 by the ambient sound determiner 610 of FIG. 4. However, it may be directly detected using the soundproof ear-covering detector 134 described with reference to FIG. 2. In addition, if it is determined that there is no bias in the ambient sound in step S204, the controller 125 issues an instruction to the user to cover his/her ears. However, the controller 125 may issue an instruction to cover the ears regardless of presence of the bias in the ambient sound (that is, even if the volume obstructing state is not resolved in step S201). Further, when the user covers his/her ears, the ambient sound detected in, for example, the first peripheral sound microphone 131 or the like may be superimposed on the output audio signal (VO) with the volume adjusted. In this case, it is possible to prevent the ambient sound from being completely inaudible.

Further, if it is determined that there is a bias in the ambient sound, the controller 125 issues an instruction to the user to change the orientation of his/her head. However, at this time, the controller 125 may also issue an instruction including the orientation of the head or the like. Specifically, for example, based on detection results of the first to third peripheral sound microphones 131 to 133, the controller 125 may determine a direction of arrival of the ambient sound, calculate the orientation of the head so as to move away from the direction of arrival, and, in cooperation with the sensor device (such as the gyro sensor 115 or the geomagnetic sensor 116), guide the user to face such an orientation.

FIG. 6 shows the configuration example around the controller 125 with respect to step S202 (that is, resuming sound emission) of FIG. 5. FIG. 6 shows the controller 125, the pair of headphones 122, and an audio library 622. The controller 125 comprises a voice assistant processor 620 and an audio output processor 621. Here, the voice assistant processor 620, the audio output processor 621 and the pair of headphones 122 constitute an audio output interface 602 configured to generate the output audio signal, convert the generated output audio signal into the audio for output, and emit the audio for output toward the user.

The voice assistant processor 620 serves as a function that responds to the user's request via voice interaction with the user, and generates audio text data which is the source of the sound at this time. The audio library 622 includes waveform data representing each audio, and is held in, for example, the memory 128 of FIG. 2. The audio output processor 621 synthesizes the audio text data from the voice assistant processor 620 with the waveform data from the audio library 622 to generate the output audio signal (VO). The pair of headphones 122 converts the output audio signal (VO) into the audio for output, and emits the audio for output toward the user.

Here, after the controller 125 instructs the audio output interface to interrupt sound emission, if it is determined that the state in which the ambient sound is not preventing the audio for output from being heard is occurring in step S201 of FIG. 5, the controller 125 issues the resume instruction (RES) to the audio output interface 602 in step S202. In response to the resume instruction (RES), the audio output interface 602 resumes sound emission by going back to a point prior to interrupt. Specifically, for example, the audio output interface 602 resumes sound emission by going back to a beginning of a sentence that was interrupted, resumes sound emission by going back to a punctuation mark prior to the interrupted point or by going back to a previous phrase, or resumes sound emission by going back a predetermined fixed number of characters or words.

In the process of generating the audio text data, the voice assistant processor 620 recognizes a sentence unit, a phrase unit, a position of the punctuation mark or the like, and sequentially stores the generated audio text data in a buffer (such as the memory 128 of FIG. 2). In addition, the audio output processor 621 sequentially stores the generated output audio signal (VO) corresponding to the audio text data in the buffer. Therefore, based on a timing in which the interrupt instruction (INT) is received from the controller 125 (ambient sound determiner 610 of FIG. 4), the audio output interface 602 can recognize an interruption point such as the interrupted sentence, phrase, a section between punctuation marks or the like. Thereafter, when the audio output interface 602 receives the resume instruction (RES) from the controller 125 (ambient sound determiner 610 of FIG. 4), the audio output interface 602 can resume sound emission by going back to the point prior to interrupt based on the recognized interruption point.

As a specific example, assume a case where the audio output interface 602 emits the sentence "The Tokyo area will be expecting cloudy then sunny skies tonight". When the audio output interface 602 receives the interrupt instruction (INT) while emitting, for example, the portion "cloudy then sunny skies", and then receives the resume instruction (RES), the audio output interface 602 goes back to the beginning of the sentence and resumes sound emission from "The", or resumes sound emission from the portion "cloudy then sunny skies".

Note that the object to be controlled for interrupting or resuming sound emission is, for example, audio or the like from the voice assistant processor 620 that may cause a problem if the user misses hearing it. Audio that may not cause any particular problem if the user misses hearing it such as music from a music player may be excluded from being controlled. In addition, the volume level (LOx) of the output audio signal (VO) is input to the audio output interface 602 of FIG. 6 in response to an instruction by, for example, the user via the input controller 400 (see FIG. 2). The audio output interface 602 performs sound emission at a volume according to the volume level (LOx). The volume level (LOx) is also used in the ambient sound determiner 610 shown in FIG. 4.

Figure 7:
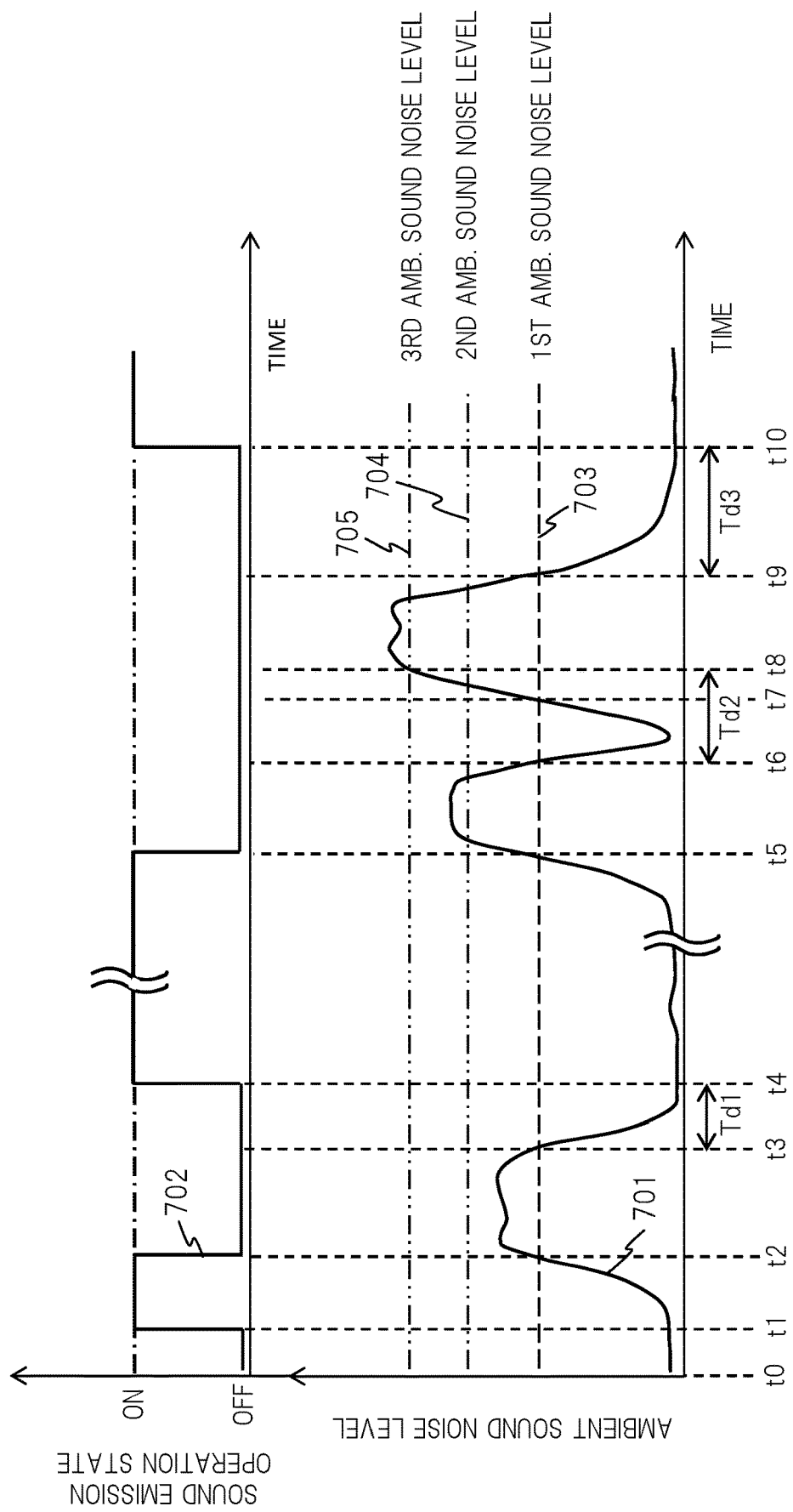
FIG. 7 is an explanatory diagram showing an operation example when a delay time is added at the time of resuming sound emission in FIG. 4.

FIG. 7 is an explanatory diagram showing an operation example when the delay time is added at the time of resuming sound emission in FIG. 4 (step S202). FIG. 7 shows a relationship between an ambient sound noise level and the sound emission operation of the output audio signal. In FIG. 7, the controller 125 starts emitting the output audio signal at time t1 when an ambient sound noise level 701 is sufficiently low, and accordingly, a sound emission operation state 702 is turned ON (operation execution). Thereafter, when the ambient sound noise level 701 becomes high and becomes greater than or equal to a first ambient sound noise level 703 corresponding to the threshold level (THx) of FIG. 4 at time t2, the controller 125 determines that the state in which the ambient sound is preventing the audio for output from being heard is occurring, and interrupts sound emission. Accordingly, the sound emission operation state 702 is turned OFF (operation stop).

Thereafter, the ambient sound noise level 701 is maintained in a state that is greater than or equal to the first ambient sound noise level 703 and less than or equal to a second ambient sound noise level 704 that is greater than the first ambient sound noise level 703, and then becomes less than the first ambient sound noise level 703 at time t3. In response, the controller 125 does not immediately issue the resume instruction (RES) to the audio output interface, but issues the resume instruction (RES) at time t4 after a predetermined period Td1 according to the volume level of the input audio signal immediately prior to time t3 (that is, immediately prior to the state in which the audio is not prevented from being heard is occurring) has passed. Here, the volume level of the input audio signal becomes greater than or equal to the first ambient sound noise level 703 and less than or equal to the second ambient sound noise level 704. In response to the resume instruction (RES) at time t4, the audio output interface resumes sound emission, and accordingly, the sound emission operation state 702 is turned ON (operation execution).

Thereafter, the ambient sound noise level 701 becomes greater than or equal to the first ambient sound noise level 703 at time t5, and accordingly, the sound emission operation state 702 is turned OFF. Then, the ambient sound noise level 701 is maintained in a state that is greater than or equal to the second ambient sound noise level 704 and less than or equal to a third ambient sound noise level 705 that is greater than the second ambient sound noise level 704 during a period of time t5 to time t6, and becomes less than the first ambient sound noise level 703 at time t6. In response, the controller 125 issues the resume instruction (RES) to the audio output interface after a predetermined period Td2 according to the volume level of the input audio signal immediately prior to time t6 (that is, the volume level greater than or equal to the second ambient sound noise level 704 and less than or equal to the third ambient sound noise level 705) has passed. Here, the corresponding volume level is greater than the volume level corresponding to the period Td1, whereby the period Td2 becomes longer than the period Td1.

Note that, in the example of FIG. 7, the ambient sound noise level 701 becomes high again at time t7 prior to time t8 in which the predetermined period Td2 has passed, and is greater than the first ambient sound noise level 703. Thus, the resume instruction (RES) is not issued, and the audio output interface maintains the interrupted state of sound emission. After time t7, the ambient sound noise level 701 is maintained in a state that is greater than or equal to the third ambient sound noise level 705, and becomes less than the first ambient sound noise level 703 at time t9. In response, the controller 125 issues the resume instruction (RES) to the audio output interface at time t10 after a predetermined period Td3 (>Td2) according to the volume level of the input audio signal immediately prior to time t9 (that is, greater than or equal to the third ambient sound noise level 705) has passed. In response to the resume instruction (RES) at time t10, the audio output interface resumes sound emission.

In general, the user may experience a period in which his/her hearing ability decreases after a large ambient sound.

This period in which hearing ability decreases becomes longer as the volume level of the ambient sound becomes higher. Therefore, performing the control as shown in FIG. 7 allows the controller 125 to reliably avoid the period in which hearing ability decreases and perform sound emission even if this period changes according to the volume level of the ambient sound, and allows the user to hear the audio for output in a good hearing state regardless of the volume level of the ambient sound. Note that, in the example of FIG. 7, the volume level of the ambient sound is divided into 3 stages. However, the volume level can be further divided into smaller stages, or can use a method in which the predetermined period continuously changes according to the volume level. Further, when resuming the sound emission operation, the volume level of the output audio signal may be controlled to be slightly increased.

Control Processing [2] of Sound Emission Operation

Figure 8:
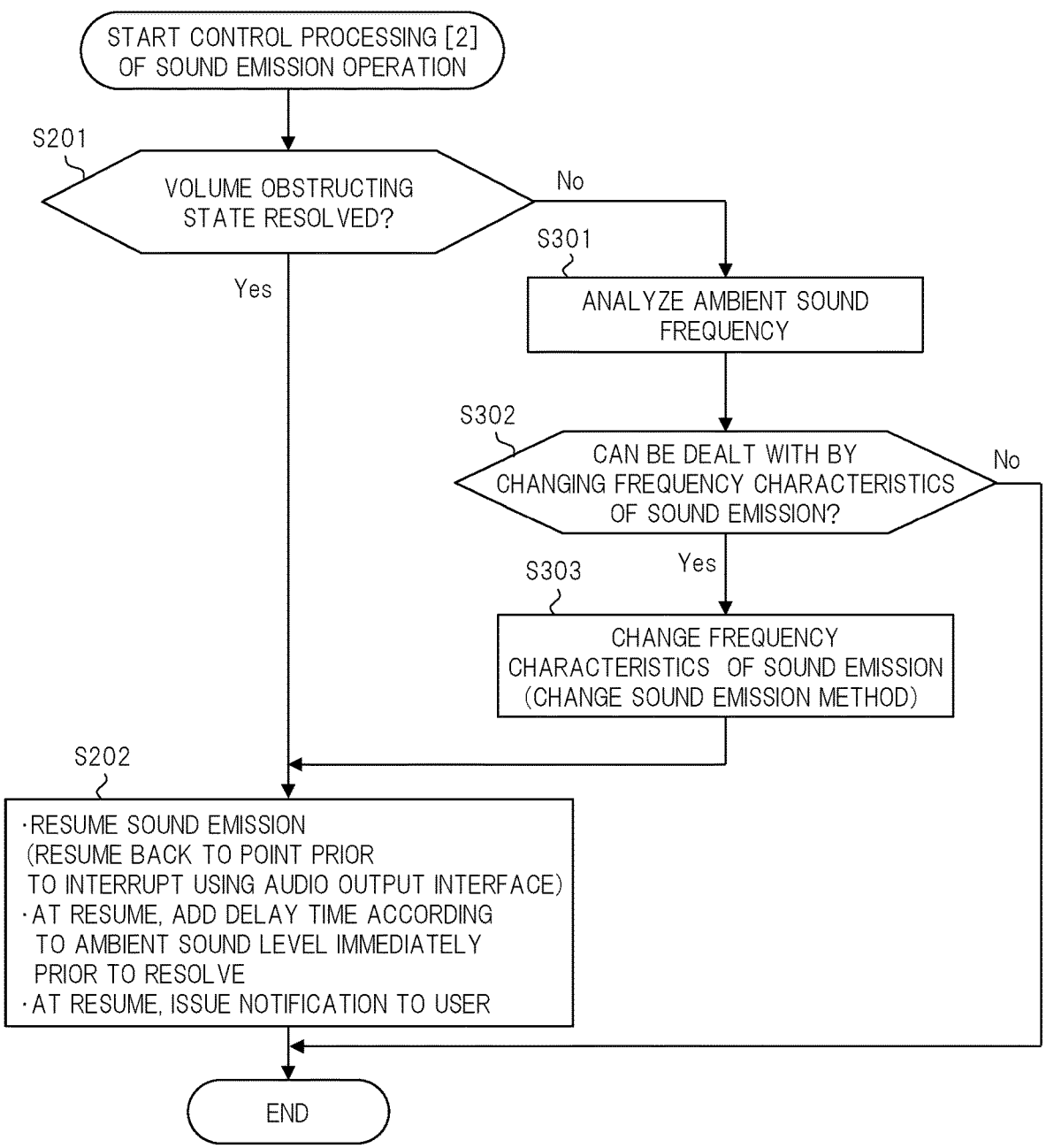
FIG. 8 is a flowchart showing an example of detailed processing contents of the control processing of the sound emission operation in FIG. 3 that differ from those of FIG. 5.

FIG. 8 is a flowchart showing an example of detailed processing contents of the control processing of the sound emission operation in FIG. 3 that differ from those of FIG. 5. FIG. 8 shows the processing contents of the control processing (step S110) of the sound emission operation that differ from those of FIG. 5 and are performed while sound emission is interrupted in FIG. 3, and shows one example of the processing contents of a control processing [2]. In FIG. 5, the controller 125 allows the user to perform various actions to take countermeasures against the ambient sound. In FIG. 8, the controller 125 changes the sound emission method (specifically, changes frequency characteristics) to take countermeasures against the ambient sound without any action of the user.

In FIG. 8, the controller 125 determines whether or not the volume obstructing state is resolved, as in the case of step S201 of FIG. 5, and if it is determined that the volume obstructing state is resolved, the controller 125 resumes sound emission, adds the delay time, and notifies the user, as in the case of step S202 of FIG. 5. On the other hand, in step S201, if it is determined that the volume obstructing state is still occurring, the controller 125 uses, for example, the audio input processor 611 of FIG. 4 to analyze the frequency characteristics of the input audio signal (VI) corresponding to the ambient sound (step S301).

Subsequently, based on analysis results of the frequency characteristics in step S301, the controller 125 determines whether or not the issue can be dealt with by changing the frequency characteristics of the output audio signal to be emitted (step S302). That is, the controller 125 determines whether or not the state in which the ambient sound is preventing the audio for output from being heard is occurring can be resolved by changing the sound emission method, although the volume obstructing state cannot be resolved in terms of the volume level determined in step S201 of FIG. 9 or step S103 of FIG. 3.

If it is determined that the issue can be dealt with by changing the frequency characteristics in step S302, the controller 125 changes the frequency characteristics of the output audio signal to be emitted (step S303), proceeds to step S202, resumes sound emission, adds the delay time, notifies the user, and ends the process. In the subsequent control cycle, the sound emission operation continues in the order of steps S101, S102, S103, S104, and S108 of FIG. 3 with the changed frequency characteristics.

In addition, if the volume level of the ambient sound decreases and the volume obstructing state is resolved in the process of continuing the sound emission operation with the changed frequency characteristics, the change in the frequency characteristics is canceled in the order of steps S103, S106 and S107 of FIG. 3, and returns to the default frequency characteristics. Then, the sound emission operation continues in the order of steps S101, S102, S103, S106 and S108 of FIG. 3. On the other hand, if it is determined that the issue cannot be dealt with by changing the frequency characteristics (that is, changing the sound emission method) in step S302, the controller 125 ends the process. As a result, a state in which sound emission is interrupted continues until the volume obstructing state is resolved.

Hereinafter, an example of a specific method regarding the change in the frequency characteristics in steps S301 to S303 will be described. First, the controller 125 (such as the audio output processor 621 of FIG. 6) has a plurality of frequency characteristics (such as fundamental frequency) applicable to the output audio signal (VO) in advance. In step 301, the controller 125 analyzes the frequency characteristics of the input audio signal to recognize the frequency characteristics (such as fundamental frequency) of the input audio signal.

Then, the controller 125 issues an instruction to the audio output interface 621 to select, from among the plurality of frequency characteristics applicable to the output audio signal (VO), the frequency characteristic whose similarity to the frequency characteristic of the input audio signal is lower than a predetermined reference value (step S303). Specifically, for example, the controller 125 causes the audio output interface 621 to select the fundamental frequency of the output audio signal (VO) that is distant from the fundamental frequency of the input audio signal by the reference value or more.

In this manner, the frequency characteristic of the output audio signal is changed to allow the user to suitably hear the emitted output audio signal even if a large ambient sound is present. However, if there is no frequency characteristic among the plurality of frequency characteristics applicable to the output audio signal whose similarity to the frequency characteristic of the input audio signal is lower than the reference value, it is determined that the issue cannot be dealt with by changing the frequency characteristics in step S302, and sound emission is not resumed.

Note that it is possible for the controller 125 to, for example, selectively execute one of the control processing [2] shown in FIG. 8 and the control processing [1] shown in FIG. 5 according to the settings, or execute the control processing [2] shown in FIG. 8 and then the control processing [1] shown in FIG. 5. Specifically, for example, if it is determined that the issue cannot be dealt with by changing the frequency characteristics in step S302 of FIG. 8, the controller 125 may execute the control processing [1] of FIG. 5 and request a predetermined action to the user.

Control Processing [3] of Sound Emission Operation

Figure 9:
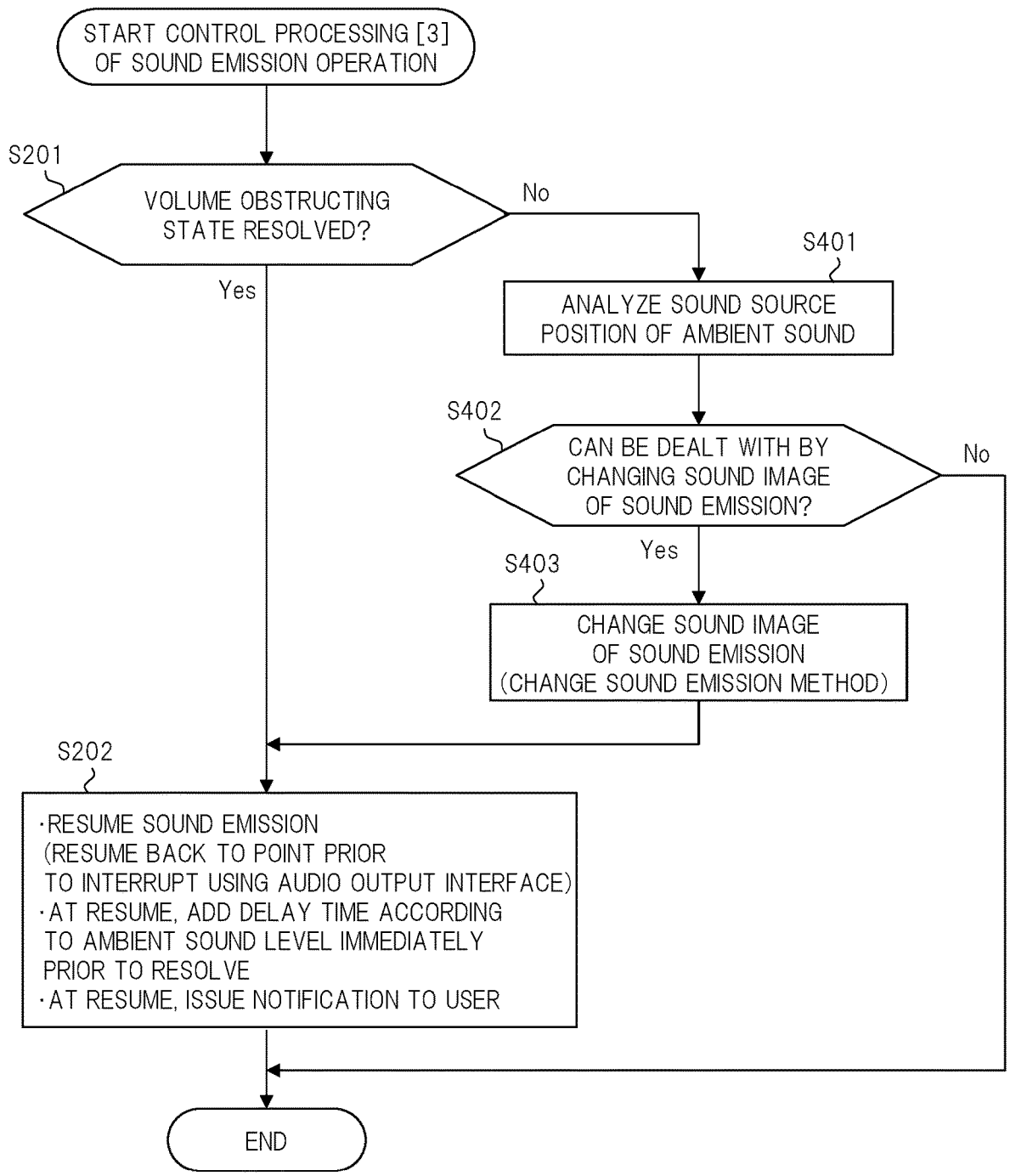
FIG. 9 is a flowchart showing an example of detailed processing contents of the control processing of the sound emission operation in FIG. 3 that differ from those of FIG. 8.

FIG. 9 is a flowchart showing an example of detailed processing contents of the control processing of the sound emission operation in FIG. 3 that differ from those of FIG. 8. FIG. 9 shows the processing contents of a control processing [3] modified from the control processing [2] of FIG. 8. In FIG. 9, the controller 125 changes the sound emission method to take a countermeasure against the ambient sound without any action of the user as in the case of FIG. 8.

However, unlike the case of FIG. 8, a countermeasure is taken by changing a sound image of the audio for output to be emitted.

In FIG. 9, the processes in steps S301 to S303 in FIG. 8 are replaced by the processes in steps S401 to S403. In FIG. 9, if it is determined that the volume obstructing state is not resolved in step S201, the controller 125 analyzes a position of a sound source of the ambient sound (step S401). Specifically, for example, the controller 125 uses the audio input processor 611 of FIG. 4 to determine the position of the sound source of the ambient sound based on the volume level, a delay difference or the like of the left and right input audio signals (VI) from the second and third peripheral sound microphones 132 and 133.

Subsequently, based on an analysis result of the position of the sound source of the ambient sound in step S401, the controller 125 determines whether or not the issue can be dealt with by changing the sound image of the audio for output to be emitted (step S402). That is, the controller 125 determines whether or not the state in which the ambient sound is preventing the audio for output from being heard is occurring can be resolved by changing the sound emission method. If it is determined that the issue can be dealt with by changing the sound image of the audio for output in step S402, the controller 125 changes the sound image of the audio for output (step S403), then proceeds to step S202, resumes sound emission, adds the delay time, notifies the user, and ends the process. On the other hand, if it is determined that the issue cannot be dealt with by changing the sound image of the audio for output in step S402, the controller 125 ends the process.

Specifically, the controller 125 instructs the audio output interface to generate the left and right output audio signals in step S403, so that a position of the sound image of the audio for output is distant from the position of the sound source of the ambient sound by a predetermined reference value or more. In response, for example, the audio output processing circuitry 621 of FIG. 6 controls the volume level of the left and right output audio signals, the delay difference or the like to control the sound image of the audio for output to be emitted from the left and right headphones 122*a* and 122*b*. At this time, for example, if the position of the sound source of the ambient sound is diagonally to the front-left, the position of the sound image of the audio for output is set diagonally to the back-right or the like.

In this manner, the sound image of the audio for output is changed to allow the user to suitably hear the emitted audio for output even if a large ambient sound is present. In addition, if it is determined that the issue cannot be dealt with by changing the sound image of the audio for output in step S402, or specifically, if it is not possible to create the position of the sound image that is distant from the position of the sound source of the ambient sound by the reference value or more, the controller 125 ends the process. As a result, the state in which sound emission is interrupted continues until the volume obstructing state is resolved.

Note that it is possible for the controller 125 to, for example, selectively execute one of the control processing [3] shown in FIG. 9 and the control processing [2] shown in FIG. 8 according to the settings, or execute the control processing [3] shown in FIG. 9 before or after the control processing [2] shown in FIG. 8 and before the control processing [1] shown in FIG. 5. Specifically, for example, if it is determined that the issue cannot be dealt with by changing the sound emission method in both step S402 of FIG. 9 and step 302 of FIG. 8, the controller 125 may execute the control processing [1] of FIG. 5 and request a predetermined action to the user.

Other Operations of the Controller

As another operation example, if it is determined that the state in which the ambient sound is preventing the audio for output from being heard is occurring, the controller 125 may instruct the audio output interface to insert and emit a fixed output audio signal representing a word that draws the user's attention at the beginning of the generated output audio signal. Specifically, for example, the controller 125 issues such an instruction when notifying the user by the audio in step S105 of FIG. 3, or when resuming sound emission after changing the sound emission method in FIG. 8 or 9. In this manner, a word that draws the user's attention is inserted at the beginning of the output audio signal to allow the user to be clearly aware of the fact that the ambient sound is increased and that it would be difficult to hear the emitted audio for output. In addition, selective attention of a cocktail party effect allows the user to hear the emitted sound with ease. An example of a word that draws the user's attention includes the user's name registered in the apparatus in advance.

Further, as another operation example, if it is determined that the state in which the ambient sound is preventing the audio for output from being heard is occurring, the controller 125 may perform a switching process to display the output audio signal from inside the head-mountable information processing apparatus on the display 119 as characters instead of emitting the audio for output. At this time, the controller 125 displays characters by going back to a point before interrupt, as in the case when resuming sound emission. This allows the head-mountable information processing apparatus to transmit predetermined information to the user via vision, although it cannot transmit the information via hearing.

Main Effects of First Embodiment

As described above, the head-mountable information processing apparatus of the first embodiment is mainly used to allow the user to reliably hear a desired sound even if the ambient sound unnecessary for the user is present. In addition, the apparatus allows the user to hear the desired sound with ease even if the ambient sound unnecessary for the user is present.

In detail, when a loud ambient sound occurs, enters the ears and prevents the emitted output audio signal from inside the head-mountable information processing apparatus from being heard, sound emission is interrupted to prevent the user from missing the audio for output. In addition, when the ambient sound becomes low enough to not prevent the audio for output from being heard, sound emission is resumed by going back to a point before interrupt to allow the user to hear the audio for output with ease without missing it. In particular, this allows the user to reliably hear the audio that may be problematic if missed, such as the audio for output from the voice assistant.

In addition, even in a case where a loud ambient sound enters the ear and temporarily reduces the hearing ability of the ear, waiting for a time required for the hearing ability to recover and then resuming sound emission allows the user to reliably hear the desired sound with ease. Further, changing the sound emission method as necessary such as changing the frequency characteristics or the sound image with respect to the audio for output, or requesting an action to the user such as covering his/her ears allows the user to reliably hear the desired sound with ease even if the ambient sound is still present. In addition, notifying the user via display, audio or vibration at the time of interrupting or resuming sound emission allows the usability to improve.

Here, the sound emission operation is controlled according to the ambient sound. However, there may be a case where the user does not desire such a control of the sound emission operation depending on the contents of the head-mountable information processing apparatus. Therefore, for example, the user may set, for each content, whether or not to control the sound emission operation with respect to the main body 100. The main body 100 may select, for each content, whether or not to control the sound emission operation according to the user settings.

Second Embodiment

Details of Controller

In a second embodiment, the controller 125 controls the sound emission operation by reflecting the state of the user (such as physical/mental state) or the state of the user's surroundings (such as occurrence of a dangerous situation), unlike the state of the ambient sound described in the first embodiment. Generally, in FIG. 2, the sensor device 151 in the main body 100 and the sensor device in each of the wearable terminals 200 and 300 detect the state of the user or the state of the user's surroundings.

Based on detection results of the sensor devices, the user state determiner 123 determines whether or not the state of the user or the state of the user's surroundings is a state suitable for hearing the audio for output. Based on a determination result of the user state determiner 123, if it is determined that the state is suitable for hearing the audio for output, the controller 125 causes the audio output interface (such as headphones 122) to perform sound emission, and if it is determined that the state is not suitable for hearing the audio for output, the controller 125 instructs the audio output interface to interrupt sound emission. Hereinafter, details thereof will be described.

Figure 10:
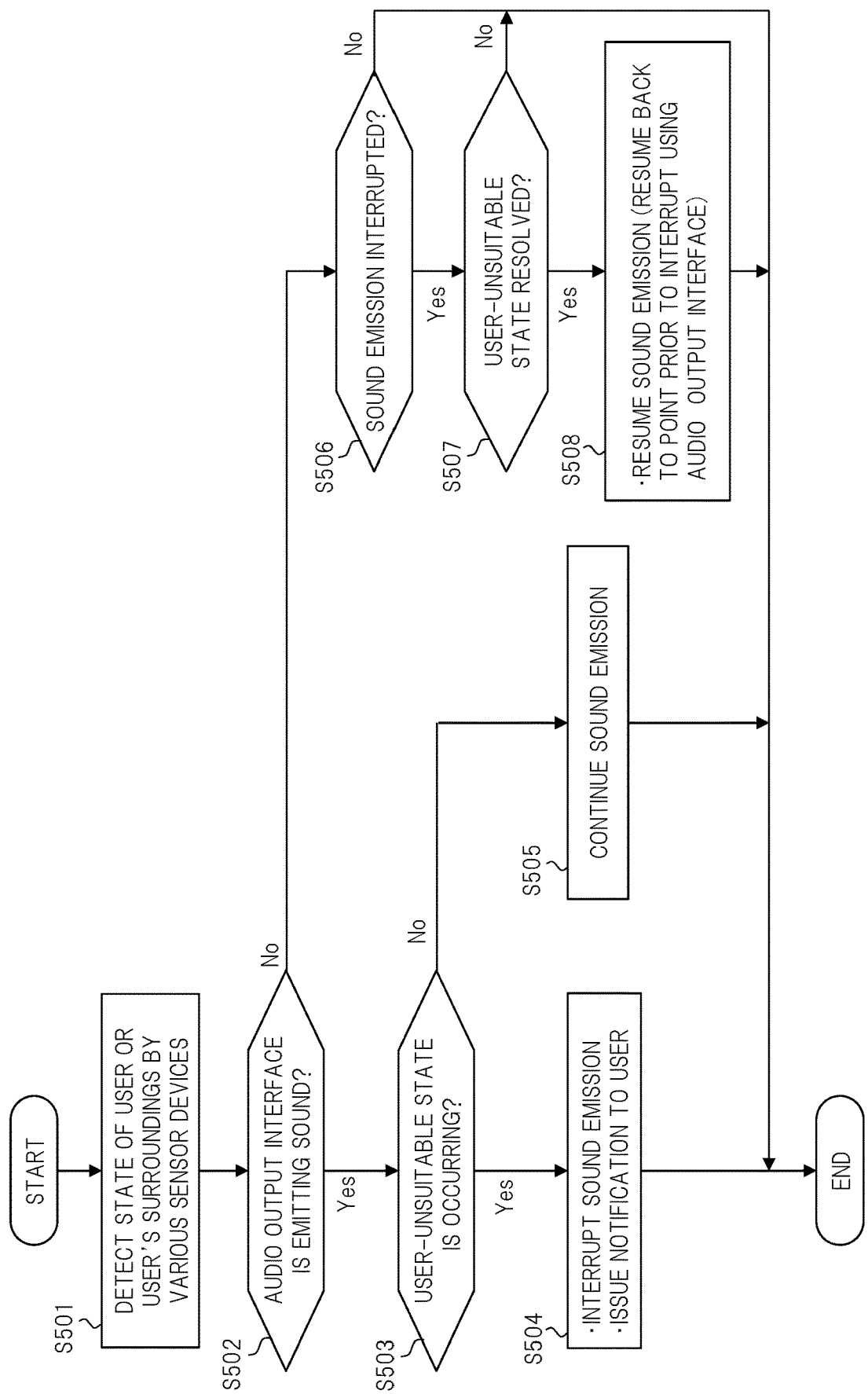
FIG. 10 is a flowchart showing an example of detailed processing contents of the controller of FIG. 2 in the head-mountable information processing apparatus according to a second embodiment of the present invention.

FIG. 10 is a flowchart showing an example of detailed processing contents of the controller of FIG. 2 in the head-mountable information processing apparatus according to the second embodiment of the present invention. The controller 125 repeatedly executes the flow shown in FIG. 10 at a predetermined control cycle. In FIG. 10, the controller 125 uses the user state determiner 123 to detect the state of the user or the state of the user's surroundings with various sensor devices (step S501).

Next, the controller 125 determines whether or not the audio output interface (headphones 122 or the like) is emitting the audio for output (step S502). Based on a detection result in step S501, if it is determined that the audio for output is being emitted in step S502, the controller 125 uses the user state determiner 123 to determine whether or not the state of the user or the state of the user's surroundings is a state suitable for hearing the audio for output (step S503). In the present specification, the state in which the state of the user or the state of the user's surroundings is not suitable for hearing the audio for output is also referred to as a user-unsuitable state.

If it is determined that the user-unsuitable state is occurring in step S503, the controller 125 instructs the audio output interface to interrupt sound emission (step S504). Further, in step S504, the controller 125 uses the notice display on the display 119, the tactile vibration by the vibration generators 124, 202 and 302, or the vocal sound by the audio output interface (headphones 122) to notify the user of the fact that sound emission is being interrupted, and ends the process. On the other hand, if it is determined that the user-unsuitable state is not occurring in step S503, the controller 125 continues sound emission by the audio output interface, and ends the process (step S505).

If it is determined that the audio for output is not being emitted in step S502, the controller 125 determines whether or not the audio output interface is interrupting sound emission (step S506). If it is determined that sound emission is not interrupted in step S506, the controller 125 ends the process. On the other hand, if it is determined that sound emission is interrupted in step S506, the controller 125 determines whether or not the user-unsuitable state is resolved (step S507).

If it is determined that the user-unsuitable state is resolved in step S507 (that is, if it is determined that the state is suitable for hearing the audio for output), the controller 125 issues the resume instruction (RES) to instruct the audio output interface to resume sound emission, as in the case of the first embodiment described with reference to FIG. 4. In response to the resume instruction (RES), the audio output interface resumes sound emission by going back to a point prior to interrupt (step S508). In addition, in step S508, the controller 125 uses the notice display on the display 119, the tactile vibration by the vibration generators 124, 202 and 302, or the vocal sound from the audio output interface (headphones 122) to notify the user of the fact that sound emission is resuming, and ends the process. In the subsequent control cycle, the sound emission operation continues in the order of steps S501, S502, S503 and S505 of FIG. 10.

Details of User-Unsuitable State

FIG. 11 is a table describing examples of user-unsuitable states in FIG. 10. FIG. 11 shows specific examples of situations in which it is determined that the user-unsuitable state is occurring in steps S503 and S507 of FIG. 10. Here, seven different situations (1) to (7) are shown. Situation (1) is a situation in which the user is considered to be paying attention to virtual reality (VR) space information or augmented reality (AR) space information on the display 119.

Specifically, for example, the user state determiner 123 detects a position of the user's eye gaze based on the right eye gaze sensor 112 and the left eye gaze sensor 113 instep S501, and obtains a display position of the virtual space information or the real space information from the virtual space information generation processor 141 or the camera 111 of FIG. 2. Then, the user state determiner 123 determines whether or not a time ratio in which the position of the user's eye gaze matches the display position of the virtual space information or the real space information is greater than or equal to a predetermined reference value. If it is determined that the matching time ratio is greater than or equal to the predetermined reference value, the user state determiner 123 considers that the user is paying attention to the virtual space information or the real space information, and in steps S503 and S507, determines that the state is not suitable for hearing the audio for output (in other words, the user-unsuitable state is occurring).

Situation (2) is a situation in which the user is considered to be making rapid eye movement. Specifically, for example, based on a detection result of each of the eye gaze sensors 112 and 113 in step S501, the user state determiner 123 determines whether or not the number of times the user's eye gaze changes within a predetermined time is greater than or equal to a predetermined reference value. In general, when a person moves his/her eye gaze from one viewpoint to another, a rapid eye rotation called a saccade occurs, and an occurrence of this saccade is determined here. If it is determined that the number of times the user's eye gaze changes is greater than or equal to the predetermined reference value, the user state determiner 123 considers that the saccade is occurring, and determines that the state is not suitable for hearing the audio for output in steps S503 and S507.

Situation (3) is a situation in which the user is considered to be not clearly conscious. Specifically, for example, based on the detection result of each of the eye gaze sensors 112 and 113 in step S501, the user state determiner 123 determines whether or not the number of times the user's eye gaze changes within the predetermined time is less than or equal to a predetermined reference value. If it is determined that the number of times the user's eye gaze changes is less than or equal to the predetermined reference value, the user is considered to be drowsy and not clearly conscious. If it is determined that the user is not clearly conscious, the user state determiner 123 determines that the state is not suitable for hearing the audio for output in steps S503 and S507.

Situation (4) is a situation in which the user's head is moving significantly. Specifically, for example, based on a detection result of the acceleration sensor 114, the gyro sensor (angular velocity sensor) 115 or the geomagnetic sensor 116 in step S501, the user state determiner 123 determines whether or not the user's head has moved a predetermined reference amount or more at a predetermined reference speed or more. If the user's head is moving significantly such as when the user is in danger, it is possible that some kind of abnormality is occurring in an external environment of the user's surroundings, and the user's visual or auditory attention may be directed thereto. If it is determined that the user's head is moving significantly, the user state determiner 123 determines that the state is not suitable for hearing the audio for output in steps S503 and S507 so as to not interfere with the user's focus concentration.

Situation (5) is a situation in which the user's physical condition has rapidly changed. Specifically, for example, based on a detection result of the heart rate sensor 201 or the blood pressure sensor 301 in step S501, the user state determiner 123 determines whether or not a temporal rate of change (such as a rate of increase) of the user's heart rate or the blood pressure is greater than or equal to a predetermined reference value. If the heart rate or the blood pressure rises rapidly, it is possible that a sudden change in the user's physical/mental state is occurring, and the user may not be able to pay attention to hearing. If it is determined that a change in the user's physical condition is occurring, the user state determiner 123 determines that the state is not suitable for hearing the audio for output in steps S503 and S507.

Note that, in FIGS. 1 and 2, the heart rate is detected by the heart rate sensor 201 of the chest-mounting type wearable terminal 200 in close contact with the chest where it can be detected most accurately, and the blood pressure is detected by the blood pressure sensor 301 of the wristband type wearable terminal 300 in close contact with the arm where it can be easily detected. However, the heart rate and the blood pressure are not particularly limited to be detected in this manner, and may be obtained by, for example, communication from an AI (Artificial Intelligence) watch or the like. In addition, the obtained information is not limited to the heart rate and the blood pressure, and can be any biometric information that can detect the user's physical/mental state.

Situation (6) is a situation in which the user is having a conversation with another person. Specifically, in step S501, the user state determiner 123 detects audio by the first peripheral sound microphone 131 and the vocal sound microphone 121, and detects eye movements by each of the eye gaze sensors 112 and 113. Based on the detected sound and eye movements, the user state determiner 123 determines where the user's consciousness is, and determines whether or not the user is facing the other person or is talking on the phone. At this time, the user state determiner 123 may recognize a presence of another person based on a captured result of the camera 111, or may recognize a telephone conversation based on a telephone function when the main body 100 is equipped with such a function. If it is determined that the user is having a conversation with another person, the user state determiner 123 determines that the state is not suitable for hearing the audio for output in steps S503 and S507.

Situation (7) is a situation in which an approaching object is present in the user's surroundings. Specifically, in step S501, based on a detection result of the peripheral object detection sensor 118, the user state determiner 123 detects a distance and relative speed of an object such as a vehicle, a person or an animal in the user's surroundings to detect whether or not an approaching object is present within a certain range around the user.

If it is determined that an approaching object is present within the certain range around the user, the user state determiner 123 assumes that the user's visual or auditory attention is directed toward the object, and determines that the state is not suitable for hearing the audio for output in steps S503 and S507. In addition, in steps S503 and S507, if the user state determiner 123 determines that the state is not suitable for hearing the audio for output based on the peripheral object detection sensor 118, the controller 125 instructs the audio output interface to emit a warning sound indicating danger toward the user.

Note that the user state determiner 123 may, for example, define ranges for detecting an approaching object in two stages: a danger range located around the user and a caution range located outside the danger range. For example, if it is determined that the approaching object is present in the caution range, the controller 125 performs a control to emit the audio for output from a direction opposite to a direction in which the approaching object is present, and notifies the user of the sound emission operation by display, sound or vibration. In this case, if there is an approaching object in the caution range, the user can hear the audio for output in a state in which a disturbance noise caused by the sound from the approaching object is reduced. Conversely, the controller 125 may emit the audio for output from the direction in which the approaching object is present. In this case, the user can easily recognize the direction of the approaching object.

In the above-described manner, the user state determiner 123 determines whether or not the state of the user or the state of the user's surroundings is a state suitable for hearing the audio for output (in other words, whether or not the user-unsuitable state is occurring). Based on this determination result, if it is determined that the state is suitable for hearing the audio for output (if it is determined that the user-unsuitable state is not occurring), the controller 125 causes the audio output interface to perform sound emission, and if it is determined that the state is not suitable for hearing the audio for output (if the user-unsuitable state is occurring), the controller 125 instructs the audio output interface to interrupt sound emission.

As another example of the user-unsuitable state, the user state determiner 123 may use the temperature/humidity sensor 117 that detects the temperature and humidity in the user's surroundings to determine whether or not the user-unsuitable state is occurring. Specifically, if it is determined that a temporal rate of change of the temperature or the humidity is greater than or equal to a reference value, the user state determiner 123 may determine that the user-unsuitable state is occurring. The sensor device that detects state of the user's surroundings is not limited to the temperature/humidity sensor 117, and it is possible to use a barometric pressure sensor that detects air pressure.

Main Effects of Second Embodiment

As described above, the head-mountable information processing apparatus of the second embodiment is mainly used to allow the user to reliably hear a desired sound by reflecting the state of the user or the state of the user's surroundings. In addition, the apparatus allows the user to hear the desired sound with ease by reflecting the state of the user or the state of the user's surroundings.

In detail, if it is determined that the state of the user or the state of the user's surroundings is not suitable for hearing the audio for output, as shown in situations (1) to (7) of FIG. 11, the apparatus is controlled to interrupt the sound emission operation even if the user is requesting the sound emission operation. In this manner, the user can reliably hear the audio for output without missing it. If it is determined that the state of the user or the state of the user's surroundings is a state suitable for hearing the audio for output, as in the case of the first embodiment, sound emission is resumed by going back to a point prior to interrupt. In this manner, the user can reliably hear the audio for output with ease.

In addition, notifying the user at the time of interrupting or resuming the sound emission operation allows the usability to improve, as in the case of the first embodiment. Further, regarding situation (7), controlling the sound emission operation according to a magnitude of the approaching object allows the user to hear the audio for output more easily. At this time, if the user is in danger by the approaching object, controlling the assistant sound to not emit sound other than an alert or a warning can ensure the user's safety and allows the user to reliably hear the desired sound.

Note that, in a situation where, for example, the user is not clearly conscious as described in situation (3), the main body 100 may perform a process in which light is provided to the user's eyes or in which two or more flashing lights are displayed in the user's field of view. In this manner, the user can switch to an awake state in which the brain is awake and the user is clearly conscious. The controller 125 detects this awake state via the user state determiner 123 to resume the sound emission operation.

Third Embodiment

Overview of Head-Mountable Information Processing Apparatus

Figure 12:
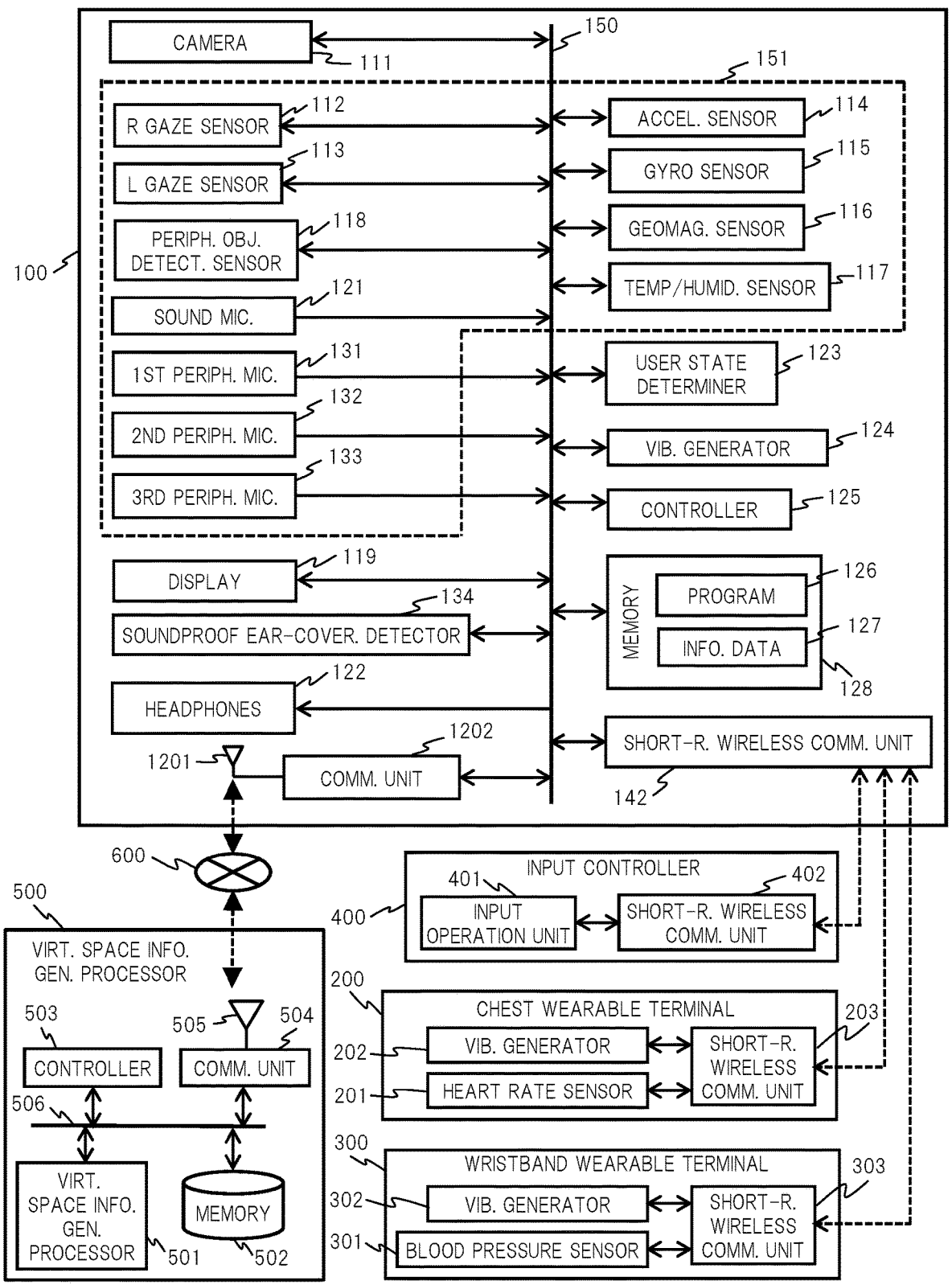
FIG. 12 is a block diagram showing a schematic configuration example of the head-mountable information processing apparatus according to a third embodiment of the present invention.

FIG. 12 is a block diagram showing a schematic configuration example of the head-mountable information processing apparatus according to a third embodiment of the present invention. Compared to the configuration example shown in FIG. 2, the head-mountable information processing apparatus shown in FIG. 12 is a configuration example in which the virtual space information generation processor 141 in the main body 100 of FIG. 2 is separated outside the main body 100 and serves as a separate apparatus.

In FIG. 12, a virtual space information generation server 500 generates the virtual space information or the like, and transmits and receives the generated virtual space information to and from the main body 100 via an external network 600. The main body 100 comprises a transmitting/receiving antenna 1201 and a communication unit 1202, and transmits and receives the virtual space information or the like to and from the virtual space information generation server 500.

The virtual space information generation server 500 comprises a virtual space information generation processor 501, a memory 502, a controller 503, a communication unit 504, and a transmitting/receiving antenna 505. These components are connected to one another via a bus 506. The virtual space information generation processor 501 generates the virtual space information in which a virtual space that differs from a real space is expressed by an image or a sound. The memory 502 is a flash memory or the like, and stores the virtual space information generated by the virtual space information generation processor 501 and various programs used by the controller 503. The communication unit 504 is a communication interface that performs communication with the main body 100 via the transmitting/receiving antenna 505 and the external network 600.

As described above, another server apparatus separated from the main body 100 is used to generate the virtual space information, and the main body 100 obtains the virtual space information via communication, so that the amount of information in the virtual space can be increased to a large scale. In addition, hardware and software resources of the main body 100 can be reduced.

Note that, with respect to the configuration example shown in FIGS. 2 and 12, the heart rate sensor 201 in the chest-mounting type wearable terminal 200, the blood pressure sensor 301 in the wristband type wearable terminal 300, and the input operation unit 401 in the input controller 400 may be incorporated in the main body 100. The heart rate sensor 201 can detect the heart rate while being worn in close contact with the head, and the blood pressure sensor 301 can detect the blood pressure at a head artery just below the scalp while being worn in close contact with the head.

In addition, the input operation unit 401 may be installed at a position in the main body 100 where the user can easily perform the input operation. Alternatively, the user may vocalize a sound indicating the input operation, and the vocal sound microphone 121 may collect the sound and incorporate the input operation information. In addition, the input operation information may be incorporated by displaying an input operation screen on the display 119 and using a position on the input operation screen to which the eye gaze detected by each of the eye gaze sensors 112 and 113 is directed. The input operation information may also be incorporated by displaying a pointer on the input operation screen and having the user specify by an operation of his/her hand or the like. Using a voice or display for the input operation allows the usability to further improve.

Note that the present invention is not limited to the foregoing embodiments and includes various modifications. For example, the foregoing embodiments have been described in detail such that the description of the present invention is easily understandable, and are not necessarily limited to comprise all of the configurations described above. In addition, a portion of the configuration of one of the embodiments can be replaced with the configuration of another embodiment. Further, the configuration of one of the embodiments can be added to the configuration of another embodiment. Furthermore, other configurations may be added to, may be omitted from or may replace a portion of the configuration of each of the embodiments.

In addition, each of the above-described configurations, functions, processors, processing means or the like may be realized in hardware by designing some or all of the above in integrated circuitry. In addition, each of the above-described configuration, functions or the like may be realized in software by a processor interpreting and executing a program that realizes each of the functions. Information of programs, tables, files or the like that realizes each of the functions can be placed in a memory, in a storage device such a hard disk, SSD (Solid State Drive) or the like, or in a storage medium such as an IC card, an SD card, a DVD or the like.

Note that the present application includes control lines and information lines that are considered necessary to describe the present invention, and does not necessarily include all of the control lines and information lines for the product. In fact, it may be considered that all of the components are connected to one another.

LIST OF REFERENCE SIGNS

100: main body of head-mountable information processing apparatus (head-mountable display)
111: camera
112: right eye gaze sensor
113: left eye gaze sensor
114: acceleration sensor
115: gyro sensor
116: geomagnetic sensor
117: temperature/humidity sensor
118: peripheral object detection sensor
119: display
121: vocal sound microphone
122: headphones
123: user state determiner
124, 202, 302: vibration generator
125, 503: controller
128, 502: memory
131: first peripheral sound microphone
132: second peripheral sound microphone
133: third peripheral sound microphone
134: soundproof ear-covering detector
141: virtual space information generation processor
142, 203, 303, 402: short-range wireless communication unit
151: sensor device
200: chest-mounting type wearable terminal
201: heart rate sensor
300: wristband type wearable terminal
301: blood pressure sensor
400: input controller
401: input operation unit
500: virtual space information generation server
501: virtual space information generation processor
600: external network
601: audio input interface
602: audio output interface
610: ambient sound determiner
611: audio input processor
615: threshold generator
616: threshold table
617: comparator
620: voice assistant processor
621: audio output processor
622: audio library

The invention claimed is:

1. A head-mountable information processing apparatus worn on a user's head and having a function for viewing images or hearing audio, the head-mountable information processing apparatus comprising:
   an audio input interface worn in the vicinity of the user's ear, and being configured to collect ambient sound that occurs outside the head-mountable information processing apparatus and enters the ear, and convert the ambient sound into an input audio signal;
   an audio output interface configured to generate an output audio signal, convert the generated output audio signal into an audio for output, and emit the audio for output toward the user, and
   a controller configured to control an operation of the head-mountable information processing apparatus,
   wherein the controller is configured to:
      based on a volume level of the input audio signal from the audio input interface and a volume level of the output audio signal from the audio output interface, determine whether a state in which the ambient sound is preventing the audio for output from being heard is occurring,
      upon determining that a state in which the ambient sound is not preventing the audio for output from being heard is occurring, cause the audio output interface to perform sound emission,
      upon determining that the state in which the ambient sound is preventing the audio for output from being heard is occurring, instruct the audio output interface to interrupt sound emission, and
      after the audio output interface is instructed to interrupt sound emission, upon determining that the state in which the ambient sound is not preventing the audio for output from being heard is occurring, instruct the audio output interface to resume sound emission after a predetermined period according to the volume level of the input audio signal immediately prior to the state in which the ambient sound is not preventing the audio for output from being heard is occurring has passed.

2. The head-mountable information processing apparatus according to claim 1,
   wherein the controller has:
      a threshold generator configured to generate a threshold level according to the volume level of the output audio signal; and
      a comparator configured to compare the volume level of the input audio signal and the threshold level to determine whether or not to instruct the audio output interface to interrupt sound emission.

3. The head-mountable information processing apparatus according to claim 2,
   wherein,
   in response to the resume instruction, the audio output interface resumes sound emission by going back to a point prior to interrupt.

4. The head-mountable information processing apparatus according to claim 3,
   wherein, in response to the resume instruction, the audio output interface resumes sound emission by going back to a beginning of a sentence that was interrupted.

5. The head-mountable information processing apparatus according to claim 1, wherein the controller controls a sound emission operation for the output audio signal from a voice assistant that responds to the user's request via voice interaction with the user.

6. A head-mountable information processing apparatus worn on a user's head and having a function for viewing images or hearing audio, the head-mountable information processing apparatus comprising:
- an audio input interface worn in the vicinity of the user's ear, and being configured to collect ambient sound that occurs outside the head-mountable information processing apparatus and enters the ear, and convert the ambient sound into an input audio signal;
- an audio output interface configured to generate an output audio signal, convert the generated output audio signal into an audio for output, and emit the audio for output toward the user,
- a display configured to display predetermined information to the user, and
- a controller configured to control an operation of the head-mountable information processing apparatus,
- wherein the controller is configured to:
  - based on a volume level of the input audio signal from the audio input interface and a volume level of the output audio signal from the audio output interface, determine whether a state in which the ambient sound is preventing the audio for output from being heard is occurring,
  - upon determining that a state in which the ambient sound is not preventing the audio for output from being heard is occurring, cause the audio output interface to perform sound emission,
  - upon determining that the state in which the ambient sound is preventing the audio for output from being heard is occurring, instruct the audio output interface to interrupt sound emission, and use the display to issue an instruction to the user to cover their ears.

7. The head-mountable information processing apparatus according to claim 6,
- wherein the controller has:
  - a threshold generator configured to generate a threshold level according to the volume level of the output audio signal; and
  - a comparator configured to compare the volume level of the input audio signal and the threshold level to determine whether to instruct the audio output interface to interrupt sound emission.

8. The head-mountable information processing apparatus according to claim 6,
- wherein, after the controller instructs the audio output interface to interrupt sound emission, upon determining that the state in which the ambient sound is not preventing the audio for output from being heard is occurring, the controller instructs the audio output interface to resume sound emission, and
- in response to the resume instruction, the audio output interface resumes sound emission by going back to a point prior to interrupt.

9. The head-mountable information processing apparatus according to claim 6,
- wherein, after the controller instructs the audio output interface to interrupt sound emission, upon determining that the state in which the ambient sound is not preventing the audio for output from being heard is occurring, the controller instructs the audio output interface to resume sound emission, and
- in response to the resume instruction, the audio output interface resumes sound emission by going back to a beginning of a sentence that was interrupted.

10. The head-mountable information processing apparatus according to claim 6,
- wherein the controller controls a sound emission operation for the output audio signal from a voice assistant that responds to the user's request via voice interaction with the user.

11. A head-mountable information processing apparatus worn on a user's head and having a function for viewing images or hearing audio, the head-mountable information processing apparatus comprising:
- an audio input interface worn in the vicinity of the user's ear, and being configured to collect ambient sound that occurs outside the head-mountable information processing apparatus and enters the ear, and convert the ambient sound into an input audio signal;
- an audio output interface configured to generate an output audio signal, convert the generated output audio signal into an audio for output, and emit the audio for output toward the user,
- a display configured to display predetermined information to user, and
- a controller configured to control an operation of the head-mountable information processing apparatus,
- wherein the controller is configured to:
  - based on a volume level of the input audio signal from the audio input interface and a volume level of the output audio signal from the audio output interface, determine whether a state in which the ambient sound is preventing the audio for output from being heard is occurring,
  - upon determining that a state in which the ambient sound is not preventing the audio for output from being heard is occurring, cause the audio output interface to perform sound emission, and
  - upon determining that the state in which the ambient sound is preventing the audio for output from being heard is occurring, instruct the audio output interface to interrupt sound emission,
- wherein the audio input interface is worn in the vicinity of each of the user's left and right ears, respectively collects left and right ambient sounds that enter the left and right ears, and respectively converts the left and right ambient sounds into left and right input audio signals, and
- wherein after the controller instructs the audio output interface to interrupt sound emission, the controller determines whether or not there is a bias of a predetermined reference value or more in the volume levels of the left and right input audio signals, and upon determining there is a bias, the controller uses the display to instruct the user to change an orientation of the user's head.

12. The head-mountable information processing apparatus according to claim 11,
- wherein the controller has:
  - a threshold generator configured to generate a threshold level according to the volume level of the output audio signal; and
  - a comparator configured to compare the volume level of the input audio signal and the threshold level to determine whether to instruct the audio output interface to interrupt sound emission.

13. The head-mountable information processing apparatus according to claim 11, wherein, after the controller instructs the audio output interface to interrupt sound emission, upon determining that the state in which the ambient sound is not preventing the audio for output from being heard is occurring, the controller instructs the audio output interface to resume sound emission, and in response to the resume instruction, the audio output interface resumes sound emission by going back to a point prior to interrupt.

14. The head-mountable information processing apparatus according to claim 11, wherein, after the controller instructs the audio output interface to interrupt sound emission, upon determining that the state in which the ambient sound is not preventing the audio for output from being heard is occurring, the controller instructs the audio output interface to resume sound emission, and in response to the resume instruction, the audio output interface resumes sound emission by going back to a beginning of a sentence that was interrupted.

15. The head-mountable information processing apparatus according to claim 11, wherein the controller controls a sound emission operation for the output audio signal from a voice assistant that responds to the user's request via voice interaction with the user.

* * * * *